(12) United States Patent
Watanabe et al.

(10) Patent No.: US 8,293,819 B2
(45) Date of Patent: Oct. 23, 2012

(54) METHOD FOR PRODUCING PARTICLES AND PARTICLES

(75) Inventors: Kohei Watanabe, Chofu (JP); Takeshi Miyazaki, Yokohama (JP); Yasuhiko Tabata, Kyoto (JP)

(73) Assignees: Canon Kabushiki Kaisha, Tokyo (JP); Medgel Corporation, Kyoto-shi (JP)

( * ) Notice: Subject to any disclaimer, the term of this patent is extended or adjusted under 35 U.S.C. 154(b) by 689 days.

(21) Appl. No.: 12/443,094

(22) PCT Filed: Nov. 22, 2007

(86) PCT No.: PCT/JP2007/073128
§ 371 (c)(1),
(2), (4) Date: Mar. 26, 2009

(87) PCT Pub. No.: WO2008/062908
PCT Pub. Date: May 29, 2008

(65) Prior Publication Data
US 2010/0092778 A1    Apr. 15, 2010

(30) Foreign Application Priority Data
Nov. 24, 2006  (JP) ................................. 2006-317184

(51) Int. Cl.
*C08J 3/00* (2006.01)
(52) U.S. Cl. ........................................ 523/326; 523/336
(58) Field of Classification Search .................. 523/326, 523/336
See application file for complete search history.

(56) References Cited

U.S. PATENT DOCUMENTS

| | | | |
|---|---|---|---|
| 5,264,553 A | 11/1993 | Hou et al. | |
| 5,270,445 A | 12/1993 | Hou et al. | |
| 5,326,484 A | 7/1994 | Nakashima et al. | |
| 5,358,822 A | 10/1994 | Hou et al. | |
| 5,376,347 A | 12/1994 | Ipponmatsu et al. | |
| 5,976,574 A | 11/1999 | Gordon et al. | |
| 5,985,248 A | 11/1999 | Gordon et al. | |
| 6,001,336 A | 12/1999 | Gordon et al. | |
| 6,068,857 A | 5/2000 | Weitschies et al. | |
| 6,077,543 A | 6/2000 | Gordon et al. | |
| 6,284,280 B1 | 9/2001 | Weitschies et al. | |
| 6,365,190 B1 | 4/2002 | Gordon et al. | |
| 6,572,893 B2 | 6/2003 | Gordon et al. | |
| 2003/0203036 A1 | 10/2003 | Gordon et al. | |
| 2007/0026083 A1* | 2/2007 | Doney | 424/490 |

FOREIGN PATENT DOCUMENTS

| | | |
|---|---|---|
| EP | 0 528 201 A2 | 2/1993 |
| EP | 0 546 174 A1 | 6/1993 |
| JP | 54-012329 A | 1/1979 |
| JP | 56-074130 A | 6/1981 |
| JP | 4-275339 A | 9/1992 |
| JP | 5-023565 A | 2/1993 |
| JP | 5-505643 A | 8/1993 |
| JP | 2733729 B | 1/1998 |
| JP | 2000-005593 A | 1/2000 |
| JP | 2001-507702 A | 6/2001 |
| JP | 2001-232178 A | 8/2001 |
| JP | 2003-071261 A | 3/2003 |
| JP | 2004-012402 A | 1/2004 |
| JP | 2004-067883 A | 3/2004 |
| WO | 92/13027 A1 | 8/1992 |
| WO | 95/07072 A2 | 3/1995 |
| WO | 98/29098 A1 | 7/1998 |

OTHER PUBLICATIONS

Shao-Hong Li et al., "In Vitro Characteristics of Poly(Lactic-Co-Glycolic Acid) Microspheres Incorporating Gelatin Particles Loading Basic Fibroblast Growth Factor," 27(6) Acta Pharmacologica Sinica 754-59 (Jun. 2006).
Mengyan Li et al., "Co-Electrospun Poly(Lactide-Co-Glycolide), Gelatin, and Elastin Blends for Tissue Engineering Scaffolds," 79(4) J. Biomed. Mater. Res. A. 963-73 (Aug. 2006).
Kenneth J. Widder et al., "Magnetic Microspheres: A Vehicle for Selective Targeting of Drugs," 20 Pharmac. Ther. 377-95 (1983).

* cited by examiner

*Primary Examiner* — Edward Cain
(74) *Attorney, Agent, or Firm* — Fitzpatrick, Cella, Harper & Scinto

(57) ABSTRACT

A method is provided for producing particles which is capable of producing particles in simple and easy steps. The objective is to provide with a high yield particles having a homogeneous particle diameter and a superior dispersibility in liquid. The method includes (1) preparing an aqueous solution containing one or more polymer; and (2) introducing the aqueous solution as droplets into a solvent capable of dissolving water by 1 mass % or more and less than 50 mass % to form the polymer into dispersed particles in the mixture of the aqueous solution and the solvent in the mixture of the aqueous solution and the solvent.

23 Claims, 2 Drawing Sheets

METHOD FOR PRODUCING PARTICLES AND PARTICLES

TECHNICAL FIELD

The present invention relates to a method for producing particles and to the particles. Described in more detail, the present invention relates to a method for producing particles in which polymer particles containing polymer material are easily produced. The present invention also relates to the particles.

BACKGROUND ART

In various fields, there has been a demand for the development of a method for easily producing particles having various properties.

For the method of producing polymer microparticles, there are methods for solidifying polymers in liquid or gas. Examples of such methods include (1) interface polymerization method, (2) phase separation method (3) in-liquid drying method (4) solvent extraction method (5) spray dry method (6) orifice method and the like. The methods will be described below.

(1) Interface Polymerization Method

The interface polymerization method, which uses a polymerization reaction, is an encapsulation method in which the wall membrane of the capsule is formed with the polymerization reaction of monomers. This method is a method which takes advantage of the phenomenon of a polymer film being achieved through a polymerization reaction at the interface of the dispersion phase of two solutions which do not mix. However, there are problems with this method, such as with the selection of the combination of monomers, there are restrictions in handling. Also, a purification step is necessary, in which unreacted monomers are removed after the formation of particles.

(2) Phase Separation Method

The phase separation method is a method for making particles in which, with a polymer that is dissolved in a solvent, a solvent that precipitates the polymer is added, or the temperature is manipulated so that the polymer becomes insoluble in order to conduct phase separation of the polymer to accelerate the generation of a uniform nucleus and to control the cohesion step. With this method, the production time is long, and the steps are complicated, and only low concentrations of microcapsule dispersion solutions are obtained. During the production process, cohesion between particles occurs easily. In addition, there are problems where because mineral oil or plant oil is used for the dispersion media, there is difficulty in removal and washing, and the like.

(3) Liquid Drying Methods

In the in-liquid drying method, a membrane material solution, which is an emulsion or dispersion of a core material, is dispersed into a medium in which the solution does not dissolve to form an emulsion, and a dispersion solution is obtained. Next, by raising the temperature or decreasing the pressure, the solvent is gradually removed, and the polymer is deposited on the surface. With this method, because the stability of the dispersion solution greatly influences the quality of the particles, a surface active agent and polymer must be added to the outermost phase. In addition, there are problems such as because the solvent removal rate influences the dispersion stability, the temperature of this process must be controlled, and the like.

(4) Solvent Extraction Method

For the solvent extraction method, first, a polymer solution in which polymer and drug are dissolved is made into microdroplets in a second solvent, which is insoluble in the polymer and which is incompatible with the polymer solution, through stirring with a homogenizer or ultrasonic treatment. Afterwards, a common solvent, which dissolves both the polymer solution and the second solvent, is added. The solvent in which the polymer is dissolved is extracted from the microdroplet to the second solvent, and the polymer is deposited to form particles. With this method, there is the problem that not only is the operation complex, but during the solvent extraction operation, the drug is transferred to the second solvent, and the amount of drug enclosed inside the final polymer material is less.

(5) Spray Dry Method

In the spray dry method, the solution of the polymer material is sprayed using high pressure gas and is dried inside a drying chamber and is recovered as dried solid particles. With this method, because spraying is conducted using high pressure gas, it is difficult to control the spray conditions accurately. The particles formed by spraying have a wide particle size distribution. As a result, the raw material that is sprayed collide and aggregate with each other, and among the particles obtained in the end, differently shaped particles are present, and there is a problem of having a large degree of variability, and the like.

(6) Orifice Method

In the orifice method, a core material is dispersed in a polymer solution, and with this solution, microcapsules are formed by passing this solution through an orifice and shaping and solidifying the polymer. As a method of forming this microcapsule, there is a method that takes advantage of the gel formation of agarose depending on the temperature. In addition, there are also methods that take advantage of the formation of an electrolyte membrane by the reaction of polyacrylic acid with polyethylene imine or the formation of a calcium alginate gel from the reaction of sodium alginate and calcium. However, in order to be able to produce reproducibly microparticles of uniform composition, there are problems because of the necessity of complicated operations such as adjustment of pH, fine adjustments of concentrations of each component and temperature control, and the like.

In addition, other methods of producing particles have also been studied.

In Japanese Patent Application Laid-Open No. H04-275339, an aqueous solution of a water-soluble protein is emulsified in an organic solvent which has a water solubility of 10 g/100 g water at 20° C. Spherical particles of water-soluble protein are produced by removing the water content from this emulsion solution. However, with this invention, there are problems in that because the water content is removed from the emulsion solution, a long drying step is necessary, and the like.

In addition, as a method for producing particles with a uniform particle size, methods which use inkjet technology have been studied. For example, in Japanese Patent Application Laid-Open No. 2000-005593, a polyamine compound and a polyisocyanate compound are separated into a water-based liquid and a dispersion medium. The water-based liquid is ejected from a droplet ejecting nozzle and is dispersed in the dispersion medium so that both phases are in contact. At the interface of both phases, a surface polymerization membrane of polyamine compound and polyisocyanate compound is formed.

In addition, in Japanese Patent Application Laid-Open No. 2001-232178, there is disclosed a method in which a liquid containing all or a portion of at least one material that forms a microcapsule is discharged from an inkjet type head into a liquid to be discharged.

In addition as an emulsification process for producing particles of uniform particle size, there are disclosed emulsification methods such as a membrane emulsification method described in Japanese Patent No. 2733729, a microchannel emulsification method described in Japanese Patent Application Laid-Open No. 2003-071261, branching microchannel method described in Japanese Patent Application Laid-Open No. 2004-012402, and the like. According to these emulsification methods, emulsions with very little unevenness can be produced, and as a result, particles of uniform particle size can be produced.

As described above, with the methods for producing polymer particles which have been disclosed up to now, if the addition of a substance for accelerating the deposition of polymers is necessary, after producing the particles, treatment such as washing and purifying and the like is necessary. In addition, if the steps for mixing or emulsifying the polymer solution in a solvent and a step for polymer deposition are separate, the emulsification is often unstable, and the emulsification drops become fused or aggregation of the polymer often occurs. As a result, for stability of the emulsion, the addition of an active agent or tight control of the stirring conditions is necessary.

With the methods for emulsification by the inkjet method, membrane emulsification method, microchannel emulsification method, and branching microchannel method, particles with uniform particle size are produced. However, in order to have a uniform particle shape with these methods, the processes for emulsification and particle formation that were conducted by stirring in the prior art are replaced by the methods described above, and otherwise these follow the particle production methods of the prior art. As a result, they still have the same problems as described above.

DISCLOSURE OF THE INVENTION

By intensive study by the present inventors, the following fact was discovered. In other words, if the solvent that is used is freely miscible (can be dissolved) in water, the water in the aqueous solution is rapidly diffused and mixed in the solvent. The polymer in the aqueous solution is deposited without entering an emulsified state. As a result, very large deposits or irregularly shaped particles are generated.

In addition, if the water content that can be dissolved in the solvent, represented by (mass of water)/(total mass of water and solvent)×100, is less than 1 mass %, the water from the droplets of aqueous solution that is emulsified in the solvent scarcely dissolves in the solvent. As a result, deposition of polymers from the emulsion does not occur, and phase separation occurs, or additional steps as in the particle production methods of the prior art become necessary.

With this, the present inventors discovered that introduction of the aqueous solution which contains a polymer into a solvent with a solubility for water of 1 mass % or more and less than 50 mass %, results in formation of particles via the following process. In other words, the present inventors discovered that the droplets of aqueous solution made into particles in the solvent enter an emulsified state for a very short period of time immediately after entering the solvent, and the water inside the droplets then rapidly move into and is dissolved in the solvent to deposit uniform polymers that have uniform dispersion and particle size.

As described above, the object of the present invention is to provide an easy and simple process for producing particles by introducing an aqueous solution containing a polymer into a solvent with a prescribed range of solubility for water. In addition, by using the production method of the present invention, particles with uniform particle size and excellent dispersion is provided at a high yield.

In order to achieve the above objects, the present invention is composed as follows.

1. A method for producing particles, comprising the steps of:

(1) preparing an aqueous solution containing one or more polymers; and (2) introducing the aqueous solution as droplets into a solvent capable of dissolving water by 1 mass % or more and less than 50 mass % to form the polymer into dispersed particles in the mixture solution of the aqueous solution and the solvent.

By using the method for producing particles of the present invention, complex procedures are eliminated, and particles of polymers are produced by a simple procedure. In addition, according to the present invention, particles are produced using only the target polymer, water, and solvent. As a result, a purification step is simplified, and in some case the purification step is unnecessary. With steps that are much easier than the prior art, polymer particles which are uniform and are stable and have excellent dispersion in liquid is produced at high yield.

BEST MODE FOR CARRYING OUT THE INVENTION

Figure 1A:
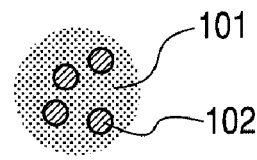
FIGS. 1A, 1B and 1C are schematic diagrams illustrating the course of particle formation in the production method of the present invention. The polymer in the aqueous solutions in FIGS. 1A, 1B and 1C are in dissolved or dispersed conditions.

The present invention is described in detail.

The solubility of water in the solvent used in the present invention is represented by the following formula (1).

$$\text{Mass of water (g)/(mass of water (g)+mass of solvent (g))} \times 100 \text{ (mass \%)} \qquad \text{Formula (1)}$$

The solubility of water in the solvent used in the present invention can be measured by the following method.

Firstly, a solvent and water are mixed in equal quantity, the mixture is stirred at a prescribed temperature for 24 hours, and then is allowed to stand to be separated. Next, the amount of water in a solvent phase is measured according to Karl Fisher's method to determine water composition in the solvent.

1. Materials Used

The materials that are used in the method for producing particles of the present invention are described.

<Polymer>

The polymers used in the present invention can be water-soluble, water-insoluble, or partially water-soluble. In addition, the polymer is not limited and can be natural or synthetic. When used in organisms, a biodegradable polymer that breaks down in the body is preferred. In addition, if used in organisms, the polymer preferably does not exhibit toxicity even with the breakdown of the polymer.

For the polymer of the present invention, preferably a water-soluble polymer is used. By using a water-soluble polymer, the difference in solubility of the water-soluble polymer in water and in the mixture solution (mixture solution of the aqueous solution and solvent) can be used to have effective deposition of the water-soluble polymer in the mixture solution.

In addition, a combination of a water-soluble polymer with a disperser of a water-insoluble polymer can be used to produce particles which contain a water-soluble polymer and a water-insoluble polymer. Because the particle contains both a hydrophilic polymer and a non-hydrophilic polymer, the non-hydrophilic polymer supporting a hydrophobic drug can be delivered while enclosed inside a hydrophilic particle. As a result, the delivery of hydrophobic drugs is possible while also maintaining the favorable cellular affinity of a hydrophilic polymer.

The water solubility of the water-soluble polymer is preferably 0.05 mass % or more and 90 mass % or less, and more preferably 0.1 mass % or more and 70 mass % or less, and more preferably 0.5 mass % or more and 50 mass % or less. By using a polymer aqueous solution with this solubility, polymer particles are obtained with high yield. In addition, the viscosity of the polymer aqueous solution does not become excessively high, and the aqueous solution is easily introduced and mixed into the solvent.

The water solubility of the polymer is represented by the following formula (2).

Mass of polymer (g)/(mass of water (g)+mass of polymer (g))×100 (mass %)    Formula (2)

The polymer used in the present invention is not particularly limited, and the following examples can be used.

Natural polymers such as polysaccharides, polyamino acids, proteins, lipids, water-soluble natural gum, nucleic acids, and their derivatives: polyethylene oxide, polypropylene oxide, polyvinyl pyrrolidone, polyvinyl alcohol, polyamidoamine, polymalic acid, poly(o-hydroxyalkyl) acrylate and methacrylate, copolymer containing hydroxyl group-containing monomer units, polyacrylic acid, polyacrylamide, polyacrylic acid copolymer, and their derivatives.

These polymers can be used singly or a plurality can be used in combination. In addition, derivatives of polymers that can be used in the present invention are preferably derivatives in which side chains of polyethylene oxide or polypropylene oxide are introduced. With this, the aggregation of particles is suppressed. The derivative of the polymer can be derivatized after the creation of the particle.

The polysaccharides that can be used as the polymer of the present invention are homoglycan (polysaccharide of a monosaccharide of glucose, fructose, mannose, galactose, galacturonic acid, glucosamine and the like), heteroglycan (polysaccharide of component sugars of glucose, fructose, mannose, galactose, arabinose, xylose, glucuronic acid, and the like).

For the polysaccharides or their derivatives described above, examples include: pullulan, xanthan gum, welan gum, rhamsan gum, succinoglycan, dextran, guar gum, tara gum, locust bean gum, ghatti gum, arabinogalactan gum, arabia gum, quince seed gum, psyllium seed gum, xanthan gum, gellan gum, tamarind gum, tragacanth gum, karaya gum, erwinia gum, scleroglucan, galactoglucan, glucomannan, inulin, levan, xylan, carrageenan, pectin, starch, fucoidan, alginic acid, agar, hyaluronate, amylose, amylopectin, glycogen, cellulose, carboxymethyl cellulose, methyl cellulose, hemicellulose, chitin, agarose, carrageenan, heparin, hyaluronic acid, pectin, xyloglucan, pullulan, curdlan, xanthan gum, gellan gum, lignin, chitosan, dextran, dextrin, carboxyalkyl chitosan, and water-soluble cellulose derivative. Pullulan and dextran are suitably used.

The polyamino acid that can be used for the polymer of the present invention has, for its basic framework, a polypeptide in which amino acids have been condensed by dehydration. For concrete examples of the component amino acids, there are no particular limitations, however examples include the amino acids and amino acid derivatives such as the 20 essential amino acids, L-ornithine, the series of α-amino acids, β-alanine, γ-amino butyrate, neutral amino acids, acidic amino acids, ω-ester of acidic amino acids, basic amino acids, N-substituted basic amino acids, and aspartic acid-L-phenylalanine dimer (aspartame), amino sulfonates such as L-cysteine acid. The α-amino acids can be an optically active material (L-form, D-form) or a racemate.

In addition, the polyamino acid can be a copolymer containing other monomer components. Examples of monomer components of the copolymer include aminocarboxylate, aminosulfonate, aminophosphonate, hydroxycarboxylate, mercaptocarbonate, mercaptosulfonate, and mercaptophosphonate.

In addition, examples also include polyvalent amine, polyvalent alcohol, polyvalent thiol, polyvalent carboxylic acid, polyvalent sulfonic acid, polyvalent phosphonic acid, polyvalent hydrazine compound, polyvalent carbamoyl compound, polyvalent sulfonamide compound, polyvalent phosphonamide compound, polyvalent epoxy compound, polyvalent isocyanate compound, polyvalent isothiocyanate compound, polyvalent aziridine compound, polyvalent carbamate compound, polyvalent carbamic acid compound, polyvalent oxazoline compound, polyvalent reactive unsaturated bond compound, and polyvalent metal. If it is a copolymer, it can be a block copolymer or random copolymer. In addition, it can be a graft.

The protein that can be used as the polymer of the present invention is not particularly limited, but known proteins, fusion proteins which combine known amino acid sequences, or proteins having artificial amino acid sequences can be used.

Examples of such proteins include proteins which construct the extracellular matrix such as fibronectin, laminin, vitronectin, fibrinogen, fibrin, collagen, and gelatin, sericin, fibroin, keratin, albumin, and casein. Derivatives of these materials in which appropriate functional groups have been introduced can also be used. In particular, because they can support materials such as various bioactive substances and drugs, gelatin and its derivatives are useful.

Gelatin can be obtained by denaturing collagen, which is collected from various parts of the body such as skin, bone, and tendon from various animals including cow, pig, and fish, or a substance that is used as collagen, by various treatments such as alkaline hydrolysis, acidic hydrolysis, and enzymatic breakdown. Gelatin that is a denatured form of a genetically engineered collagen can also be used. The characteristics of gelatin are varied depending on the material used and treatment method, but gelatin with any of these characteristics can be used as the material for the particles of the present invention.

In addition, for the polymer that can be used in the present invention, a polymer that can be stably dispersed in water (a polymer that is insoluble in water or a polymer that is partially soluble in water) can be used. For such a polymer, there are no particular limitations, but examples that are suitably used include: poly-L-lactic acid, polyD, L-lactic acid, polyglycolic acid, their copolymers, poly(aliphatic carboxylate), copolyoxalate, polycaprolactone, polydioxonene, poly(orthocarbonate), poly(acetal), poly(lactic-acid-caprolactone), polyorthoester, poly(glycolic acid-caprolactone), polyanhydride, polyphosphazine, polylactide-co-glycolide, wax, polystyrene, and polyester.

<Components other than Polymer>

The particles of the present invention contain at least one of the substances of either a bioactive substance or a labeling substance.

The bioactive substance used in the present invention is not particularly limited, but examples include anti-cancer drugs, antibiotics, thrombolytics, angiogenic factors, cell growth factors, hormones, cytokines, polypeptides having bioactivity, antipyretics, sedatives, adjuvants, anti-inflammatories such as dexamethasone, antitussives, anti-seizure agents, antihistamines, antihypertensive diuretics, diabetic treatment agents, muscle relaxants, anti-tumor agents, antidepressants, anti-allergy agents, cardiac stimulants, antiarrhythmic drugs, vasodilators, anticoagulants, narcotic antagonists, hemostatic drugs, antituberculosis drugs, lipid-lowering drugs such as pravastatin, simvastatin, fluvastatin, and atorvastatin, DNA, and RNA.

The anti-cancer agents that can be used in the present invention are not particularly limited, but examples include tegafur, doxifluridine, fluorouracil, methotrexate, mitomycin, bleomycin, etoposide, vinblastine, vincristine, irinotecan, cisplatin, and paclitaxel; those that are effective in bone cancer, bone neoplasms, myeloma, osteosarcoma include cyclophosphamide, ifosfamide, melphalan, and ranimustine; in addition, alkylating agents such as busulfan, and thiotepa; antimetabolites such as methotrexate, 6-mercaptopurine, 5-fluorouracil, cytosine arabinoside, floxuridine (FUDR), and UFT; anti-cancer antibiotics such as daunomycin, adriamycin, mitomycin, bleomycin, neocarzinostatin, and methotrexate (MTX); and plant alkaloids such as vinblastine and vincristine; and immunopotentiators such as krestin.

In addition, for the labeling substance that can be used in the present invention is not particularly limited, but dyes, fluorescent dyes, near-infrared pigment, substances labeled with radioactive isotopes, iodine compounds, barium compounds, magnetic metals, metal oxides, gases, and the like. These can be detected by various imaging techniques such as fluorescent spectroscopy, near infrared spectroscopy, scintigraphy, positron-emission tomography, nuclear magnetic resonance image, X-ray photography, and ultrasonogram.

Furthermore, the aqueous solution of the present invention can contain a water-insoluble material. The water-insoluble material used in the present invention is not particularly limited, but suitable examples include magnetic material, metal particle, metal oxide, hydrophobic bioactive substance, colorant, and hydrophobic polymer microparticle. These water-insoluble materials can be self-dispersing or they can be dispersed by a dispersant.

The method by which at least one type of substance that is selected from the group including bioactive substance, labeling substance, and water-insoluble substance is included inside the particle is not particularly limited.

For example, the aforementioned substance can be introduced by chemically grafting the substance into the polymer in advance. In addition, the aforementioned substance can be dissolved and dispersed in the aqueous solution in advance to create the particles which contain the aforementioned substance. In this case, for example, these substances are already dissolved and dispersed in the aqueous solution prepared in step (1), (a). In the next step (2), (b), a solvent that lowers the solubility of these substances is used to have these substances, together with the polymer, deposited or dispersed in the mixture solution of the aqueous solution and the solvent.

In addition, the aforementioned substances can be added in the solvent in step (2), (b). In this case, these substances and the polymer aggregate to form particles in the mixture solution of the aqueous solution and the solvent, thereby producing particles that contain the polymer and at least one substance selected from the group including bioactive substance, labeling substance, and water-insoluble substance.

Furthermore, after producing the particles, a step for supporting the aforementioned substances can also be added. After producing the particles, as a step for supporting the aforementioned substances, the particles can be soaked in the aforementioned substances, or the substances can be bound to the particles by taking advantage of electrostatic interactions, covalent bonding, or hydrophobic interactions.

In addition, a gas can be included as a labeling substance in the particles of the present invention. With particles which contain a gas as a labeling substance, ultrasonograms are possible. Gas which can be included in the particles of the present invention are not particularly limited, but in order to maintain a gaseous state while in the body, the boiling point is less than body temperature, and preferably 10° C. or less.

Stated more concretely, gas of perfluorocarbon is preferably used. Examples include octafluorocyclobutane, octafluoropropane, and hexafluoroethane. In addition, the gas used is preferably one that is insoluble in water. With this, when administered to an organism for example, it does not dissolve in body fluids such as blood, and the imaging effect can persist for a long time.

The method for including the gas in the particle can be any method, and for example, by vacuum drying the aforementioned particle, and next, injecting the gas into the depressurized chamber, the inside of the particle is thereby substituted with this gas.

When a bioactive substance, labeling substance, water-insoluble substance are included in the particle, the polymer content of the particle is preferably 0.1 mass % or more and 99.9 mass % or less, and more preferably 0.5 mass % or more and 99 mass % or less, and even more preferably 1 mass % or more and 99 mass % or less (these are all based on dry solids). In addition, the content of bioactive substance, labeling substance, and water-insoluble substance in the particle is preferably 0.001 mass % or more and 99 mass % or less, and more preferably 0.1 mass % or more and 70 mass % or less, and even more preferably 0.1 mass % or more and 50 mass % or less (these are all based on dry solids, except for gas as a labeling substance).

<Solvent>

The solvent used in the production method of the present invention is not limited as long as water can be dissolved with a solubility of 1 mass % or more and less than 50 mass %. This solubility does not represent solubility at a certain temperature, but represents the solubility of water in the solvent at the temperature of the mixture solution in which the aqueous solution and solvent are mixed in step (2), (b) of the present invention.

Because solubility is dependent on the temperature, by adjusting the temperature of the mixture solution in step (2), (b) of the present invention, the solubility of water in the solvent can be controlled to be within 1 mass % or more and less than 50 mass %, or within a desired range within 1 mass % or more and less than 50 mass %. For such a solvent, from the standpoint of ease of temperature adjustment and stability of materials used, a solvent capable of dissolving water by 1 mass % or more and less than 50 mass % at a temperature of 40° C. or less is preferred.

If the solvent is capable of dissolving water by less than 1 mass %, very little water dissolves in the solvent in step (2), (b), and as a result, it becomes difficult for the polymer to be deposited as particles in the mixture solution of the aqueous solution and the solvent. On the other hand, with a solvent capable of dissolving water by 50 mass % or more, water rapidly diffuses into the solvent and becomes mixed, and there is no emulsified state. As a result, irregular particles are formed, or coarse deposits are generated, and forming of particles is difficult.

The following are examples of solvents which can be used in the present invention which is capable of dissolving water by 1 mass % or more and less than 50 mass %.

Examples include 1-butanol, 2-butanol, isobutyl alcohol, 1-pentanol, 2-pentanol, 3-pentanol, 2-methyl-1-butanol, isopentyl alcohol, tert-pentyl alcohol, 3-methyl-2-butanol, 1-hexanol, 2-methyl-1-pentanol, 4-methyl-2-pentanol, 2-ethyl-1-butanol, 1-heptanol, 2-heptanol, 3-heptanol, 2-ethyl-1-hexanol, 3,5,5-trimethyl-1-hexanol, 1-decanol, cyclohexanol, 2-pentanone, 3-pentanone, 2-hexanone, methyl isobutyl ketone, 2-heptanone, isobutyric acid, valeric acid, isovaleric acid, acetic anhydride, methyl formate, ethyl formate, methyl acetate, ethyl acetate, propyl acetate, isopropyl acetate, butyl acetate, isobutyl acetate, sec-butyl acetate, ethylene glycol monophenyl ether, propionitrile, and triethyl amine. These solvents can be used singly, or a combination can be used.

Of these solvents, solvents which is capable of dissolving water by 7.5 mass % or more and less than 50 mass % are preferred. When the solvent capable of dissolving water by 7.5 mass % or more is used, the amount of polymer-containing aqueous solution that can be introduced into the solvent is greater, and as a result, the production yield is higher.

Examples of solvents which is capable of dissolving water by 7.5 mass % or more and less than 50 mass % include 1-butanol, 2-butanol, isobutyl alcohol, 2-pentanol, 3-pentanol, 2-methyl-1-butanol, isopentyl alcohol, tert-pentyl alcohol, 3-methyl-2-butanol, phenol, cyclohexanol, cyclohexanone, methyl ethyl ketone, isobutyric acid, valeric acid, methyl formate, ethyl formate, methyl acetate, ethylene glycol monophenyl ether, propionitrile, and triethylamine. These solvents can be used singly, or a combination can be used.

In addition, the boiling point of the solvent of the present invention is not particularly limited. If, after producing the particles, vacuum drying is conducted to remove the solvent and water, a solvent with a boiling point close to that of water is preferred.

The boiling point of the solvent is preferably 50° C. or more and 160° C. or less, and more preferably 75° C. or more and 135° C. or less. If the boiling point is too much higher than that of water, it becomes difficult to remove the solvent from the mixture solution, particularly if solvent removal is conducted by vacuum drying. On the other hand, if the boiling point is too much lower than water, the solvent will evaporate faster than the water during the production of particles or during drying, and the concentration of water in the mixture solution becomes high, and as a result, a portion of the polymer deposited as particles re-dissolve, and the particle shape can collapse.

In order to avoid such problems, during the step for drying the particles, the solvent can be replaced with a solvent that is suitable for the drying step. Examples of non-aqueous solutions that have boiling points of 75° C. or more and 135° C. or less include: 1-butanol, 2-butanol, isobutyl alcohol, 2-pentanol, 3-pentanol, 2-methyl-1-butanol, isopentyl alcohol, tert-pentyl alcohol, 3-methyl-2-butanol, methyl ethyl ketone, and triethylamine.

In addition, water can be added to the solvent beforehand. Although the amount of water to be added is not particularly limited as long as it is less than the solubility for water with respect to the solvent, an amount in the range of 10 mass % or less can be added.

In addition, salt can be added to the solvent beforehand. Although there are no particular limitations on the salt, suitable examples are sodium chloride, ammonium sulfate, and the like. By adding a salt, the deposition of polymer can be accelerated.

For the combination of various polymers and solvents, the following examples are given.

Using a combination of gelatin, dextran, or pullulan, and their derivatives for the polymer and 1-butanol, 2-butanol, isobutyl alcohol, tert-pentyl alcohol, 3-methyl-2-butanol for the solvent is especially preferred.

A combination of gelatin and its derivatives for the polymer and 1-butanol or 2-butanol for the solvent is even more preferred.

<Polymer-Containing Aqueous Solution>

When using a water-soluble polymer as the polymer for the present invention, in order to dissolve the polymer stably in the ion exchange water, various buffer solutions can be included.

In addition, a water-soluble dissolving agent can be added to the polymer-containing aqueous solution beforehand as needed.

For the water-soluble dissolving agent, for every type, preferably, 20 mass % or less is added, and more preferably, in the range of 5 mass % or less is added. The water-soluble dissolving agent can be anything as long as it dissolves in water. The following examples can be used.

Alkyl alcohols of carbon number 1-4, such as methyl alcohol, ethyl alcohol, n-propyl alcohol, isopropyl alcohol, 1-butyl alcohol, 2-butyl alcohol, and tert-butyl alcohol;

amides, such as dimethylformamide, dimethylacetamide;

ketones or ketoalcohols, such as acetone and diacetone alcohol;

ethers, such as tetrahydrofuran and dioxane;

polyalkylene glycols, such as polyethylene glycol and polypropylene glycol;

alkylene glycols containing an alkylene group with a carbon number of 2 to 6, such as ethylene glycol, propylene glycol, butylene glycol, triethylene glycol, 1,2,6-hexanetriol, thiodiglycol, hexylene glycol, and diethylene glycol;

glycerin;

a lower alkyl ether of a polyvalent alcohol, such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, and triethylene glycol monobutyl ether;

N-methyl-2-pyrrolidone, 2-pyrrolidone, and 1-dimethyl-2-imidazoline. Either one or two or more of these water-soluble dissolving agents can be selected and used as appropriate. In the present description, with regard to the aforementioned water-soluble dissolving agents, those capable of dissolving water by 1 mass % or more and less than 50 mass % are included in the "solvent" of step (2) or (b) of the production method of the present invention. Because of this, in step (2) of the first production method for particles described below, when adjusting the amount of aqueous solution introduced into the solvent so that all of the water in the aqueous solution is dissolved in the solvent, the aforementioned water-soluble dissolving agent is contained in the solvent. In addition, in the second method for producing particles described below, when mixing the aqueous solution in the solvent so that the (mass of water)/(total mass of solvent and water)×100 is equal to or less than the solubility of water in the solvent, the aforementioned water-soluble dissolving agent is contained in the solvent.

2. Method of Producing Particles

In the method for producing particles of the present invention (first and second particle production methods), the materials described in the "1. Materials used" section described above can be used. Below, the particle production method of the present invention will be described in detail.

First Method for Producing Particles

The first method for producing particles of the present invention has the following steps.

(1) preparing an aqueous solution containing one or more polymer.

(2) introducing the aqueous solution as droplets into a solvent of which solubility of water is 1 mass % or more and less than 50 mass % to form the polymer into dispersed particles in the mixture of the aqueous solution and the solvent in the mixture of the aqueous solution and the solvent.

Here, for the polymers, the polymers described in the "Polymer" section above can be used.

In addition, as components other than the polymer, bioactive substances, labeling substances, water-insoluble substances can be dissolved and dispersed in the aqueous solution. The polymer in the aqueous solution is completely or partially dissolved in the water, or is insoluble.

Figure 1B:
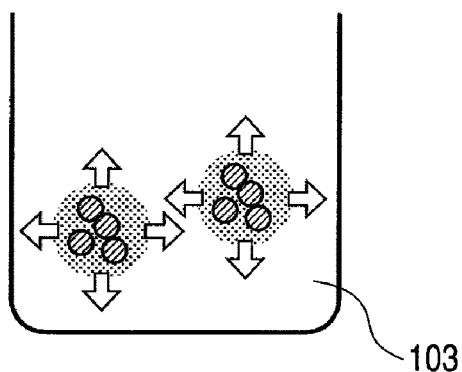
Figure 1C:
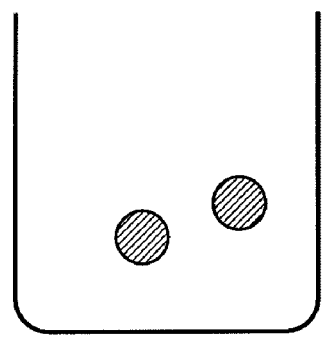

Next, in step (2), the aqueous solution is introduced into the solvent as droplets. FIGS. 1A, 1B, 1C represent this condition. The solubility of water (101) in the solvent (103) at this time is 1 mass % or more and less than 50 mass %. As a result, the droplets of aqueous solution in the solvent form an emulsified state only for a very short period of time immediately after introduction into the solvent. Afterwards, the water in the introduced aqueous solution dissolves into the solvent (FIG. 1B). With this, because the aqueous solution is introduced into the solvent as droplets, the contact surface area with the solvent is large, and the dissolving of water into the solvent occurs rapidly.

When the water (101) dissolves into the solvent (103) in this manner (FIG. 1B), the polymer (102) already contained in the aqueous solution cannot completely dissolve in the mixture solution of the aqueous solution (water) and solvent, as a result, the polymer is deposited (formed into particles) in the mixture solution (FIG. 1C). When a water-soluble polymer is used, because the polymer that is already dissolved in water is deposited, the deposited polymer particles have uniform particle properties, and there is good dispersion in the mixture solution. In addition, when a water-insoluble polymer is used, because the polymer that is already uniformly dispersed in water due to interactions with water is deposited, particles with excellent dispersion in the mixture solution are obtained. In addition, the distribution of the particle size is narrow, and particles with uniform particle size are obtained.

Furthermore, by adjusting the solubility of water in the solvent, the amount of aqueous solution added to the solvent, the solubility of the polymer in the solvent, and polymer concentration in the aqueous solution, the properties of the particles (uniformity of particle size, dispersibility of the particles, and the like) deposited in step (2) can be controlled.

In the present invention, (A) in step (2), the amount of aqueous solution introduced into the solvent is preferably adjusted to an amount in which all of the water in the aqueous solution can be dissolved in the solvent (an amount that is equal to or less than the solubility of water in the solvent). By introducing the aqueous solution into the solvent so as to satisfy the aforementioned condition (A), there is not water that does not dissolve in the solvent. As a result, the polymer that is already dissolved in the aqueous solution can be effectively deposited (formed into particles) into the mixture solution.

In the present invention (B) in step (2), the amount of aqueous solution introduced into the solvent is preferably adjusted to an amount so that the amount of polymer exceeds the amount that can be dissolved in the mixture solution (an amount exceeding the solubility of the polymer in the mixture solution). This can be achieved by adjusting the polymer concentration in the aqueous solution of step (1) and by adjusting the amount of aqueous solution added to the solvent in step (2). By introducing the aqueous solution into the solvent so that the aforementioned condition (B) is satisfied, polymer that cannot be dissolved in the mixture solution is generated. As a result, the polymer that is already dissolved in the aqueous solution can be effectively deposited (formed into particles) in the mixture solution.

More preferably, step (2) is conducted so that the aforementioned conditions (A) and (B) are satisfied. By conducting step (2) such that the aforementioned conditions (A) and (B) are satisfied, particles with excellent particle properties can be produced with high yield.

In the present invention, a formation of emulsion state of droplets, solvent elimination in emulsion droplets and deposition of polymers, which have been carried out in separate steps in the prior arts, can be carried out continuously and rapidly by means of a single solvent in one step. Further, in the present invention, it is unnecessary to employ dispersion aid, polymerization initiator, and so on.

<Mixture Solution>

In the present invention, particles are produced by introducing a polymer-containing aqueous solution into a solvent, thereby forming the polymers into dispersed particles in the mixture solution of the solvent and the aqueous solution. With this, the amount of aqueous solution introduced into the solvent is preferably an amount that is equal to or less than the solubility of water in the solvent. More preferably, the amount is equal to or less than 80% of the solubility of water in the solvent (the maximum amount that can be dissolved in the solvent). When water is introduced into the solvent at an amount close to the solubility of water in the solvent, the water that is already hydrating the polymer in step (1) is not removed adequately, and the deposition of particles of polymer is incomplete, and thereby the agglomeration of particles may occur more readily.

<Introduction Method>

In the present invention, in step (2), the polymer-containing aqueous solution is introduced into the solvent as droplets. In this case, the size of the droplets is not particularly limited, but droplets of diameter of 0.5 μm or more and 500 μm or less are preferred. When the diameter of the droplets is less than 0.5 μm, introduction of droplets into the solvent may become difficult because of air resistance. On the other hand, if the diameter of the droplets is larger than 500 μm, there can arise the problem of the droplets in the solvent fusing with other droplets. In this case, producing uniform particles becomes difficult.

In addition, after introducing the aqueous solution into the solvent as droplets, an agitating operation can be conducted if necessary. With this, the agitating operation is not particularly limited, but examples include agitation methods using a mixer such as a magnetic stirrer, intermittent shaker, propeller type agitator, turbine type agitator; colloid mill method;

homogenizer method; ultrasonic method, and the like. In the present invention, these methods can be combined and used as appropriate.

<Unit for Providing Droplets>

In the present invention, the method for introducing the polymer-containing aqueous solution into the solvent as droplets is not limited as long as small droplets are formed, but a unit for ejecting droplets can be suitably used.

The unit for ejecting droplets is preferably one that can eject droplets that have a volume of 100 nl or less per droplet, and more preferably, one that can eject droplets of 1 nl or less. For the droplet ejecting unit, examples include a micropipette, microdispenser, an ejecting device using an inkjet method in which droplets are ejected from a nozzle by using an energy generating device, mist-forming device, and the like. For the droplet ejecting unit, an ejecting device which uses the inkjet method can be suitably used from the standpoint of being made inexpensively and being able to eject small droplets.

There are no particular limitations for the inkjet method, but examples include a continuous system, electrostatic attraction inkjet system, thermal inkjet system, and piezo inkjet system. Furthermore, among the inkjet methods, the thermal inkjet method and piezo inkjet methods can be suitably used. With the ejecting device by the thermal inkjet method, it is easy to have a fine processing of the eject opening, and small droplets can be formed easily. In addition, with the ejecting device using the piezo inkjet method, because the ejecting energy is generated by the displacement of the piezo element, there is no added thermal stress on the bioactive substances, and the bioactive substances can be ejected stably.

The nozzle used in the droplet ejecting unit preferably has a nozzle diameter of 50 μm or less, and more preferably a nozzle diameter of 20 μm or less. When a droplet ejecting unit is used, the solvent is preferably left still and is not agitated.

<Microchannel Emulsion Method>

In addition, with the present invention, as a method for introducing the polymer-containing aqueous solution into the solvent as droplets, the use of membrane emulsion method, microchannel emulsion method, or a branching microchannel method, and the like are suitable.

The membrane emulsion method or microchannel emulsion method is a method of pressurizing one of two liquids using a partition having multiple small pores to penetrate this membrane, and dispersing in the other liquid. By having a uniform distribution of pore size, particles of uniform particle size can be created. The hole area of the fine pores is preferably 0.01 um$^2$ or more and 5000 um$^2$ or less, and more preferably 0.1 um$^2$ or more and 2000 um$^2$ or less. With the membrane emulsion method and microchannel emulsion method, when introducing the aqueous solution into the solvent, shear force can be applied to the solvent. Methods for applying shear force include agitating of the solvent or supplying the solvent at a constant flow at the introduction part for the aqueous solution. For the membrane emulsion method, for example, a method using the porous glass (SPG) developed by Miyazaki Prefectural Industrial Technology Center as a membrane can be suitably used. In addition for the microchannel emulsion method, a microchannel emulsion device (EPTEC Co.) and the like can be suitably used.

The branching microchannel method is a method by which the aqueous solution is introduced into the solvent by joining the flow paths of a solvent that flows in a first fluid channel at a constant speed with an aqueous solution flowing through a second fluid channel. The particle diameter can be easily controlled by the size of the channel and the flow rate.

<Recovery Method for Particles>

The polymer particles produced by the above production method can be used directly as a dispersion solution, or it can be recovered as a dry powder in which water and solvent are removed. The method for removing the water and solvent are not particularly limited. For example, after centrifuging with a centrifuge, the supernatant can be removed, heat can be provided for evaporation, or it can be dried by leaving under vacuum. These methods can be combined as appropriate.

Second Method for Producing Particles

The second method for producing particles of the present invention has the following steps.

(a) preparing an aqueous solution containing one or more polymer.

(b) mixing the aqueous solution into a solvent capable of dissolving water by 1 mass % or more and less than 50 mass % so that (mass of water)/(total mass of solvent and water)× 100 is equal to or less than the solubility of water in the solvent, to form the polymer into dispersed particles in the mixture solution of the aqueous solution and the solvent.

Step (a) above can be conducted similarly to step (1) of the aforementioned first method for producing particles.

In the present invention, (C) in step (b), the amount of aqueous solution introduced into the solvent is an amount such that (mass of water)/(total mass of solvent and water)× 100 is equal to or less than the solubility of water in the solvent. By introducing the aqueous solution into the solvent so as to satisfy the above condition (C), excess water that cannot be dissolved in the solvent does not occur. In addition, with this, the droplets of aqueous solution in the solvent in the solvent form an emulsified state for a very short period of time immediately after introduction into the solvent, and afterwards, the water in the introduced aqueous solution dissolves into the solvent.

When the water dissolves into the solvent in this manner, the polymer that is already contained in the aqueous solution does not completely dissolve in the mixture solution of the aqueous solution (water) and solvent, and as a result, the polymer is deposited (formed into particles) in the mixture solution.

When a water-soluble polymer is used, because the polymer that is already dissolved is deposited, the deposited polymer particles have uniform particle properties, and there is good dispersion in the mixture solution. In addition, when a water-insoluble polymer is used, because polymer that is uniformly dispersed in water can act as a nucleus for further deposition of polymer, particles with excellent dispersion in the mixture solution and with uniform particle size are obtained.

Furthermore, by adjusting the solubility of water in the solvent, the amount of aqueous solution added to the solvent, the solubility of the polymer in the solvent, and polymer concentration in the aqueous solution, the properties of the particles (particle size, dispersibility of the particles, and the like) deposited in step (b) can be controlled.

In the present invention, (D) in step (b), preferably, the aqueous solution is mixed into the solvent so that the amount of polymer exceeds the amount that can be dissolved in the mixture solution (an amount exceeding the solubility of the polymer in the mixture solution). By mixing the aqueous solution into the solvent so that the aforementioned condition (D) is satisfied, polymer that cannot be dissolved in the mixture solution is generated. As a result, the polymer that is already dissolved in the aqueous solution can be effectively deposited (formed into particles) in the mixture solution.

Preferably, the amount is equal to or less than 80% of the solubility of water in the solvent (the maximum amount that can be dissolved in the solvent). When water is introduced into the solvent at an amount close to the solubility of water in the solvent, the water that is already hydrating the polymer in step (b) is not removed adequately, and the deposition of particles of polymer is incomplete, and thereby the agglomeration of particles may occur more readily.

<Mixture Method>

In step (b) of the present invention, the solvent and the aqueous solution are mixed. There are no particular limitations on the mixing method of the solvent and the aqueous solution, but examples include mixing prescribed amounts of solvent and aqueous solution all at once or divided over several times, and agitating this mixture solution using known agitation methods.

The agitation method is not particularly limited, but examples include agitation methods using a mixer such as a magnetic stirrer, intermittent shaker, propeller type agitator, turbine type agitator; colloid mill method; homogenizer method; ultrasonic method, and the like. In the present invention, these methods can be combined and used as appropriate.

In addition, the mixture solution of aqueous solution and solvent can be agitated after introducing the aqueous solution into the solvent as droplets. For the method of introducing droplets into the solvent and the droplet conditions in this case, they can be conducted similarly as the first method for producing particles described above.

<Recovery Method for Particles>

This can be conducted similarly as in the first method for producing particles described above.

In the method for producing particles of the present invention (that is, the first and second methods for producing particles), magnetic particles as mentioned below can be also prepared by using an aqueous solution containing at least biodegradable polymer and magnetic material as an aqueous solution containing one or more kinds of polymers.

3. Particles

Particles can be obtained by using the first and second methods for producing particles described above. A polymer is contained in these particles. For the polymer, hydrophilic polymer and hydrophobic polymer can be contained singly, or a combination thereof can be included. In addition, other than the polymer, at least one kind of substance selected from the group including bioactive substance, labeling substance, and water-insoluble substance can be included in the particle.

The particles of the present invention obtained in this way have excellent dispersion in liquid and uniformity of particle size. The particle diameter of the particles is preferably 0.5 μm or more and 500 μm or less. By having the particle size within this range, the particles of the present invention can be suitably used for various fields.

In addition, the particle size distribution of the particles is preferably such that the ratio between the mean volume diameter and mean number diameter is 1.00 to 1.50, and more preferably 1.00 to 1.25. With particles with such a uniform particle size distribution, the particle properties can be controlled easily. Particles with uniform particle size distribution can be produced easily by using the droplet providing unit and membrane emulsion method, microchannel emulsion method, branching microchannel method, and the like that were described above to introduce droplets of uniform size.

In addition, for the method of measuring the particle diameter of the particles of the present invention, image analysis method using electron microscope images or the like, dynamic light scattering method, laser diffraction/scattering measurement method, and the like can be used. As a measuring method, image analysis with electron microscope images is particularly preferred.

<Cross-Linking of Particles>

In the method for producing particles of the present invention, a step for cross-linking the particles can be included. In order to use the particles of the present invention in a water-based environment, particularly inside a living body, the particles are cross-linked or coated so that the particles are maintained without being dissolved. Therefore, it is preferable to cross-link or coat the particles. The method for cross-linking is not particularly limited, but chemical cross-linking, electron beam cross-linking, ultraviolet cross-linking, γ-ray induced cross-linking, dehydration cross-linking, coating and the like are suitable for use. In this situation, ones that can be cross-linked by the aforementioned cross-linking methods are selected. In addition, for the extent of cross-linking, the degree of cross-linking can be chosen according to the usage objective.

When chemical cross-linking is conducted, though it is not particularly limited, a cross-linking agent can be added in advance into the solvent into which the small droplets are to be introduced in Step (2) or (b), and cross-linking can be conducted at the same time as the introduction of microdroplets. In addition, dried particles can be cross-linked by suspending in a suitable solution containing a cross-linking agent.

For the cross-linking agent, various ones can be used. For water-based cross-linking agents, there are no particular limitations, but, for example, glutaraldehyde, formaldehyde, and the like are used. In addition, for the non-water based cross-linking agent, for example, diisocyanate hexamethylene and the like are suitable for use.

In addition, the electron beam cross-linking, ultraviolet cross-linking, γ ray induced cross-linking, and dehydration cross-linking can be conducted using an electron beam irradiating device, ultraviolet irradiating device, γ-ray irradiating device, vacuum oven, respectively. The cross-linking can be selected singly as appropriate, or a combination thereof can be conducted.

4. Magnetic Particles

Below, we will describe details of the materials for constructing magnetic particles of the present invention.

<Biodegradable Polymers>

The biodegradable polymer constructing the magnetic particle of the present invention represents a polymer which can break down inside the living body. With regard to the biodegradable polymer, there are no limitations as long as the polymer has this characteristic. For example, biodegradable examples of natural polymers, such as polysaccharides, polyamino acids, proteins, lipids, nucleic acids, water-soluble natural gum, and the like or their derivatives can be used singly, or a combination thereof can be suitable for use.

For the derivatives of biodegradable polymers that can be used for the present invention, derivatives in which polyethylene oxide or polypropylene oxide is introduced as a side chain are preferred. With this, agglomeration of magnetic particles in the blood can be suppressed. The derivative of the polymer can be derived after producing the magnetic particle. In addition, when used in a living body, a polymer that does not show toxicity even after being decomposed is preferable.

<Magnetic Material>

The magnetic material of the present invention is contained in an aqueous solution. The magnetic material is not particularly limited, but, for example, metals or metal oxides with magnetic properties or an organic magnetic material can be used. Examples include, but are not limited to: various ferrites, such as triiron tetraoxide ($Fe_3O_4$), γ-iron sesquioxide ($\gamma\text{-}Fe_2O_3$), MnZn ferrite, NiZn ferrite, YFe garnet, GaFe garnet, Ba ferrite, Sr ferrite and the like; metals such as iron, manganese, cobalt, nickel, chromium, gadolinium, and the like, alloys of iron, manganese, cobalt, nickel, and the like, high crystallinity iron compound, and the like.

For example, when a biological substance is fixed to the top of the magnetic material, or when administering the magnetic material to an organism, magnetite ($Fe_3O_4$) which is suitable for organisms can be used. In addition, various ferrite compositions in which a portion of the metal element of magnetite is substituted with at least one other type of metal element are suitable for use as necessary.

Preferably, the magnetic particles of the present invention contain iron oxide as the magnetic material. By containing iron oxide, the magnetic particle of the present invention can achieve a high magnetic susceptibility.

<Microparticles>

Microparticles of the present embodiment of the following (2) contain a biodegradable polymer and magnetic material. The microparticles of the following (1) contain a biodegradable polymer, magnetic material, and at least one substance of either a bioactive substance or a labeling substance. In addition, the magnetic particles of the present invention of the following (1) and (2) are constructed by the agglomeration of these microparticles. Because of this, the breakdown of magnetic particles occurs by the loosening of the agglomeration of microparticles or by the breakdown of the microparticle itself. In the present specification, these "microparticles" include a variety of sizes from ones that are the size of molecules, or ones that are clusters of molecules that have aggregated to a certain degree, or ones that are a colloid. The particle diameter of the microparticles used in the present invention can be selected according to its use. For example, microparticles with a particle diameter of 1 nm or more and less than 500 nm are preferred. By having such a particle diameter, after breakdown, the microparticles can effectively reach the target site and location.

<Magnetic Particles>

The magnetic particles of the present invention are particles with a construction of the following (1) or (2).

(1) Magnetic particles for medical use, comprising the steps of: agglomerated microparticles containing a biodegradable polymer and a magnetic material; and at least one of either a bioactive substance and a labeling substance.

(2) Magnetic particles, comprising agglomerated microparticles containing a biodegradable polymer and a magnetic material, and having incomplete cross-link.

The magnetic particles of the above (1) contain at least one substance of either biodegradable polymer, bioactive substance and labeling substance and also contain a magnetic material. In the magnetic material of the prior art, there was low agglomeration between magnetic bodies, and it was difficult to have magnetic particles with high magnetic susceptibility through the agglomeration of each of the magnetic bodies. In contrast, because the magnetic particles of the present invention contain biodegradable polymer and a magnetic material, the magnetic bodies can agglomerate at a high density via the biodegradable polymers. As a result, the magnetic particles of the present invention can realize a higher magnetic susceptibility than microparticles of the prior art. By applying a magnetic field, the magnetic particles of the present invention can be guided efficiently to the prescribed site inside the human body.

Furthermore, these magnetic particles can be degraded under prescribed conditions. As a result, after moving the magnetic particles to a prescribed location in the human body, which have been administered into the human body, by magnetic force by providing prescribed conditions in this prescribed location, the magnetic particles can be degraded. As a result, the bioactive substance, such as drugs and the like, or the labeling substance which is contained inside the magnetic particles is released, and the function of the bioactive substance, such as a drug or the like, or the labeling substance is expressed effectively at the target location without generating side-effects in other locations.

The magnetic particles of (2) described above contain a biodegradable polymer and a magnetic material. With the magnetic material of the prior art, for example, the dispersibility in liquid was low, and it was difficult for the magnetic bodies to agglomerate with each other to make a magnetic particle with a high magnetic material density. As a result, it was difficult to obtain magnetic particles with a high magnetic susceptibility. In contrast, because the magnetic particles of the present invention contain a biodegradable polymer and a magnetic material, the biodegradable polymer has a large agglomerating action, and as a result, the magnetic bodies can agglomerate with each other at a high density. As a result, the magnetic particle of the present invention can realize a higher magnetic susceptibility as compared to the microparticles of the prior art. By applying a magnetic field, the magnetic particles of the present invention can be efficiently guided to a prescribed location.

Furthermore, this biodegradable polymer has incomplete cross-link. Because of this, by controlling the materials which construct the magnetic particles and the degree of cross-linking of the incomplete cross-linking, the conditions for degradation of the magnetic particles can be controlled. As a result, for example, with magnetic particles which have been introduced into a human body or into a production process, after moving the magnetic particles by magnetic force to the prescribed location in the human body or to a prescribed part in the process, the magnetic particles can be easily degraded by applying prescribed conditions. Furthermore, by having drugs, sensors, tracers and the like inside the magnetic particles, the function of the drug, sensor, tracer and the like can be effectively expressed at the target location without negatively affecting the human body or other parts in the production process.

Incomplete cross-linking signifies that cross-linking has not completely conducted and the magnetic particles are degradable. Stated more specifically, the degree of cross-linking represented by the following formula (I) is less than 100%.

(Cross-linked functional group)/(functional groups capable of cross-linking)×100 (%)  Formula (I)

The (cross-linked functional group), (functional groups capable of cross-linking) can be measured by measuring the IR spectrum before and after the cross-linking reaction.

The degree of cross-linking of the incomplete cross-linking is preferably 0.1% or more and 80% or less, and more preferably 1% or more and 50% or less, and even more preferably 5% or more and 35% or less, and particularly preferably 5% or more and 25% or less. By having the degree of cross-linking within this range, the magnetic particles can be effectively degraded under a certain time and under certain conditions.

In addition, the method for incomplete cross-linking is not particularly limited, but at least one type selected from the group including chemical cross-linking, dehydration cross-linking, electron beam cross-linking, ultraviolet cross-linking, γ-ray induced cross-linking, and coating is suitably used. By using these cross-linking methods, the degree of cross-linking can be easily controlled.

When chemical cross-linking is conducted, though it is not particularly limited, a cross-linking agent can be added in advance into the solvent, and while introducing microdroplets containing biodegradable polymer and magnetic material into the solvent, cross-linking of the biodegradable polymer can be conducted at the same time. In addition, dried magnetic particles can be cross-linked by suspending in a suitable solution containing a cross-linking agent. In this case, for the cross-linking agent, various ones can be used. For water-based cross-linking agents, for example, glutaraldehyde, formaldehyde, and the like are used. In addition, for the non-water based cross-linking agent, for example, diisocyanate hexamethylene and the like are suitable for use.

In addition, the electron beam cross-linking, ultraviolet cross-linking, γ ray induced cross-linking, and dehydration cross-linking can be conducted using an electron beam irradiating device, ultraviolet irradiating device, γ-ray irradiating device, vacuum oven, respectively. The cross-linking can be selected singly as appropriate, or a combination thereof can be conducted.

The magnetic particles of the aforementioned (1) and (2) preferably have a diameter of 0.5 μm or more and 500 μm or less, and more preferably 0.5 μm or more and 100 μm or less. Such a diameter of magnetic particles allows magnetic particles to effectively reach the target part and location.

In addition, the magnetic particles of the aforementioned (1) and (2) are preferably constructed so that they can breakdown with at least one type of external stimulation selected from the group including ultrasound irradiation, application of a magnetic field, and irradiation with electromagnetic waves. These external stimulations are preferably used singly or a combination of two or more methods is used together.

In addition, the materials for constructing the magnetic particles of (1) and (2) are not particularly limited, but a polyethylene oxide group or polypropylene oxide groups is preferably on the surface thereof. In order to expose the polyethylene oxide group or polypropylene oxide group on the surface in this way, when producing the magnetic particles, a biodegradable polymer in which these groups have already been grafted can be used. In addition, a polymer derivative in which polyethylene oxide group or polypropylene oxide group has been grafted can be added to the solvent.

<Functional Magnetic Particle>

The magnetic particles of the above (1) of the present invention contain at least one substance of either bioactive substance and labeling substance.

In addition, the magnetic particles of the above (2) of the present invention preferably contain at least one substance of either a bioactive substance and labeling substance.

The content of the magnetic material of the magnetic particles is preferably 0.1 mass % or more and 90 mass % or less, more preferably 1 mass % or more and 80 mass % or less, and even more preferably 5 mass % or more and 70 mass % or less (all based on dry solid form).

The content of bioactive substance in the magnetic particle is preferably 0.1 mass % or more and 90 mass % or less, and more preferably 0.5 mass % or more and 80 mass % or less, and even more preferably 1 mass % or more and 70 mass % or less (all based on dry solid form).

The content of the labeling substance in the magnetic particle is preferably 0.001 mass % or more and 90 mass % or less, and more preferably 0.01 mass % or more and 70 mass % or less, and even more preferably 0.01 mass % or more and 50 mass % or less (all based on dry solid form, with the exception of a gas as a labeling substance).

5. Method for using Magnetic Particles

In the method for using the magnetic particles of the present invention, magnetic force is generated among the magnetic particles by applying a magnetic field to the magnetic particles, and the magnetic particles are fixed at a position that corresponds to a magnetic field application unit. The magnetic particles can be guided to a predetermined place by moving the magnetic field application unit while the magnetic particles are fixed at the corresponding position of the magnetic field application unit. Since the magnetic particles of the present invention have a high magnetic susceptibility, the magnetic particles are fixed efficiently by the magnetic field application unit and can be transferred to the target place or site.

The magnetic field application unit may be a magnet, and the magnet is not particularly limited, and a localized magnetic field may be formed by an electromagnet. Further, an alnico magnet, KS steel, MK steel, new KS steel, ferrite magnet, samarium-cobalt magnet, neodymium magnet and the like may be used singly or in combination.

Also, as a method for using the magnetic particles of the present invention, the magnetic particles can be degraded by giving an external stimulus. The external stimulus of the present invention is not particularly limited, and for example, ultrasound such as convergent ultrasonic beam, magnetic field such as alternating magnetic field or electromagnetic field may be appropriately used. These external stimuli may be used singly or in combination. After transferring the magnetic particles to the target site, the magnetic particles can be degraded instantaneously or in extremely short time by giving such an external stimulus.

Also, in the method for using the magnetic particles of the present invention, the location of the magnetic particles can be determined using a magnetic resonance imaging method.

These methods for using the magnetic particles of the present invention described above may be used singly or in combination of a plurality of methods. For example, the location of the magnetic particles is determined using the nuclear magnetic resonance method, and after transferring the magnetic particles to a predetermined place, the aggregation of the magnetic particles may be dissolved by giving an external stimulus.

As to particles and magnetic particles prepared by the present invention, for example, in the medical field, drug particles are used. For the ways of administering the drug into the body, there is administration throughout the body by intravenous injection, and there is also injection into the area near the affected site. By employing particles of the present invention, side effects due to the diffusion of the drug inside the body is decreased and persistence of the drug effect can be improved. That is, the drug can be selectively delivered to the diseased area and stored at the diseased area, and the release and active time of the drug can be controlled. In particular, with anti-cancer agents, irrespective of the derivation and action, since they exhibit similar toxicity levels to cancer cells and to normal cells, side-effects are also large. By employing particles of the present invention, the above problems can be solved.

Furthermore, as to pharmaceutical products, applications as controlled-release preparations which is capable of improving long-lasting effect of drugs which previously had a short persistence of the drug effect has been studied. By employing particles of the present invention as controlled-release preparations, decrease of amount of drug, reduction of side effects, improvement in non-compliance as well as the persistence of drug effect can be expected.

Furthermore the particles of the present invention can be utilized as controlled-release preparations, which release the drug at a constant rate and which have effectively a zero-order rate of drug release. For such controlled-release preparations, oral preparations, injectable preparations, skin patches and the like are included.

With these controlled-release preparations, there are methods which deliver the drug to the affected site through the bloodstream, and in recent years, there has been a focus on methods which conduct treatment through pulmonary administration of the drug as fine particles of uniform particle size. The present invention can be applicable to this method. Furthermore, in order to prevent clogging during the delivery and in order to have a uniform persistence time of the drug-release, particles that are as uniform in size as possible are desired, and the present invention can solve this problem.

As a technique for guiding the drug produced by employing particles of the present invention to the prescribed site inside the body, there is the technique of guiding through magnetism. Although the article by K. J. Widder, A. E. Senyei (Pharmac. Ther. 20 (1983) 377-395) does not relate to drugs, a technique is disclosed in which ferrofluids that are encapsulated in particles are accumulated within a prescribed cross-section of an object via a magnetic field placed externally. With this technique, by using a magnetic field, the movement of particles is controlled, and there may be application to drugs.

Another technique for controlling the movement of fine particles using a magnet is a technique for recovering beads by a magnet using ferromagnetic beads in which a ferromagnetic substance has been added. As an example of applying this technique for the medical field, there has been proposed a method for immobilizing antibodies onto the surface of ferromagnetic beads in which a ferromagnetic powder such as iron powder or the like is added. In this method, the ferromagnetic immunobeads are placed in blood and are allowed to react with the corresponding antigens in the blood, and the antigens are immobilized on the surface of the antigen immunobeads, and the ferromagnetic immunobeads are collected by a magnet. With this technique, antigens are removed from blood or cancer cells are removed from the bone marrow.

Ferromagnetic beads are also used for transporting drugs. In other words, they can be used as therapeutic powder for a drug delivery system. In this case, the ferromagnetic beads are injected into the veins of an organism, such as a human. By externally placing a magnet or the like on the affected site, the ferromagnetic beads are guided to the affected site by magnetic guidance. One example of such a ferromagnetic bead is a medical powder in which a magnetite nucleus is enclosed in a polymer microsphere and which at the same time is supporting a drug.

In addition, as a method for releasing a drug in a human body at a prescribed site and timing, International Publication No. 95/07072 discloses active ingredient-containing microparticles which contain, in addition to an active ingredient, a gas. These particles are destroyed by diagnostic ultrasound, thereby releasing the encapsulated active ingredient.

In addition, microcapsules containing fine gas bubbles are extremely effective as ultrasonic reflectors for ultrasound diagnosis and examination. Ultrasound contrast material and the like which exhibits high contrast has been developed by creating hollow microparticles using bioabsorbable polymers.

Furthermore, in the field of agriculture, controlled-release agricultural chemicals and fertilizers, and in the field of recording materials, applications into various capsule inks have been studied.

The present invention can be applicable to these various technical fields.

For materials used in organisms, importantly, they must be capable of retaining drugs, do no harm to the organism, be broken down inside the organism and excreted. Materials which have these functions include sugars such as dextran and the like, proteins derived from organisms such as fibrin, gelatin, and the like. These are hydrophilic materials and are very suitable for organisms. In particular, gelatin from which derivatives having various isoelectric points can be prepared is often used because a wide range of drugs can be supported due to its static electrical interactions with drugs. For hydrophobic materials, polylactic acid and copolymer of polylactic acid and glycolic acid and the like are used. These materials can be used for the delivery of drugs that are different from the above hydrophilic materials because they support hydrophobic drugs which cannot be supported by static electric interactions.

Because hydrophilic material and hydrophobic material have different properties of breakdown action and mechanical strength inside the body, there has been research into complexes which use both properties. For example, in Acta Pharmacol Sin. 2006 June: 27 (6): 754-9, particles are used in which a copolymer of polylactic acid and glycolic acid, which is a hydrophobic material, covers microparticles of gelatin, which supports a drug and is a hydrophilic material. In the organism, there is a reported effect of extended release time of the drug and prevention of the breakdown of the drug. In addition, in J. Biomed. Mater. Res. A. 2006 Dec. 15; 79 (4): 963-73., a complex material of a combination of gelatin, which is a hydrophilic material, and elastin and a copolymer of polylactic acid and glycolic acid, which is a hydrophobic material, is provided. By making a complex of these materials, cross-linking is not conducted, and it does not dissolve in water, and a good cell affinity is reported. In this way, there has been a focus on materials which have the advantages of both hydrophilic material, which has a high biological affinity, and hydrophobic material, which has high mechanical strength. However, there has been difficulty in finding a simple production of particles that are a complex of hydrophilic material and hydrophobic material.

The particles prepared by the producing method of the present invention can overcome various technical problems mentioned above.

EXAMPLES

The present invention will be described in detail by referring Examples as follows. These Examples are particular examples for deeper understanding of the present invention, and the present invention is in no way limited by these particular examples. Unless otherwise indicated, "%" represents the mass standard.

<Preparation of Polymers>

Gelatin A: derived from beef bones, isoelectric point 5.0 (Nitta Gelatin Co. Ltd.)

Gelatin B: derived from pork skin, isoelectric point 9.0 (Nitta Gelatin Co. Ltd.)

Gelatin C: gelatin succinate (Nitta Gelatin Co. Ltd.)

Gelatin D: PEG Gelatin

Gelatin D described above was prepared as follows.

First, each of 10 g of gelatin A and 3.5 g of MeO-PEG-NHS (MEC-50HS (commercial name), NOF CORPORATION) was dissolved in DMSO, and the solutions were mixed, stirred at room temperature for 1 hour. Subsequently the mixture was dialyzed for 3 days and freeze dried to prepare gelatin PEG.

Gelatin E: ethylenediamine introduced gelatin

Gelatin E described above was prepared as follows.

20 g of Gelatin B was dissolved in 500 ml of phosphate buffer saline and then heated to 40° C. Next, 60 ml of ethylenediamine (Nacalai Tesque Co. Ltd.) was added to adjust pH to 5.0, and then 10 g of 1-ethyl-3-(3-dimethylaminopropyl) carbodiimide hydrochloride (Nacalai Tesque Co. Ltd.) was added. The reaction was performed for 24 hours, the mixture was dialyzed for 3 days and freeze dried to prepare ethylenediamine introduced gelatin. Resin A: styrene-acrylic acid resin (Joncryl 678 (commercial name), Johnson Polymer Co. Ltd., weight average molecular weight 8,500, acid value 215 KOH mg/g).

Pigment Resin Dispersion Solution:

| C.I. pigment red 122. | 10 parts by mass |
| Glycerin | 6 parts by mass |
| Resin A | 10 parts by mass |
| Potassium hydroxide | 0.5 parts by mass |
| Water | 74 parts by mass |

The mixture of the above composition was dispersed with a sandmill made by Kaneda Rikakogyo Co. at 1,500 rpm for 5 hours. Subsequently the dispersion solution was diluted with ion exchanged water to 5 mass % as the pigment concentration to prepare the pigment resin dispersion solution.

DNA-Gelatin Complex:

An equal volume of 0.2% gelatin E (polymer) aqueous solution and 0.2 mg/ml EGFP expressing plasmid DNA (bioactive substance) were mixed and pipetted quickly to prepare DNA-gelatin complex. Further, 5% gelatin E aqueous solution was added to adjust the final gelatin E concentration to be 1%.

PLGA Dispersion:

Polylactic acid/glycolic acid co-polymer (PLGA:lactic acid/glycolic acid mol ratio=50/50; Wako Pure Chemical Industries, Ltd.) was dissolved in chloroform at 1% (W/W) and the mixture was gradually added dropwise to 1 weight % polyvinyl alcohol (Wako Pure Chemical Industries, Ltd.) solution. The mixture was stirred for 1 hour, and PLGA dispersion was obtained by removing the solvent by an evaporator.

PLGA-Paclitaxel Dispersion:

30% polylactic acid/glycolic acid co-polymer (PLGA:lactic acid/glycolic acid mol ratio=75/25; Wako Pure Chemical Industries, Ltd.) and OregonGreen 488 labeled paclitaxel (Invitrogen Inc.) were dissolved in dichloromethane at 10% (W/W) paclitaxel/PLGA in PLGA solution. Next, the solution was gradually added dropwise to 1 weight % polyvinyl alcohol (Wako Pure Chemical Industries, Ltd.) solution. The mixture was stirred for 1 hour, and PLGA-paclitaxel dispersion was obtained by removing the solvent by an evaporator.

<Production of Particles>

Example 1

Gelatin A (polymer) was dissolved in pure water to prepare 0.5% gelatin solution (the aqueous solution of the present invention) (step (1)), and then loaded to a printhead of an inkjet printer (Pixus 950i (commercial name): Canon). Next, 100 g of 1-butanol (solvent; the solubility of water to this solvent=20 mass %) was placed in a beaker, and the beaker was placed under the printhead, and then an ejection signal was given to the printhead to eject droplets of the gelatin solution and 10 g of the solution was ejected into 1-butanol to obtain a dispersion solution of gelatin A particles (mixed solution) and at the same time gelatin A was formed into particles in this mixture (step (2)). At this time, the temperature of the mixture was kept at 20° C.

Further, after centrifuging thus obtained dispersion solution at 500 G for 5 minutes, the supernatant was removed and the precipitates were re-suspended by adding 100 ml of 1-butanol. The suspension was centrifuged again at 500 G for 5 minutes and the supernatant was removed. The precipitates were dried under reduced pressure to evaporate residual the solvent and water off, and dried particles were obtained.

When the dispersion solution of gelatin A described above was visually evaluated, neither phase separation no formation of macroaggregated material were observed in the dispersion solution. Further, after standing for 24 hours, particles were precipitated spontaneously but particles can be re-dispersed easily by stirring indicating no strong aggregation of the precipitated particles.

Figure 2:
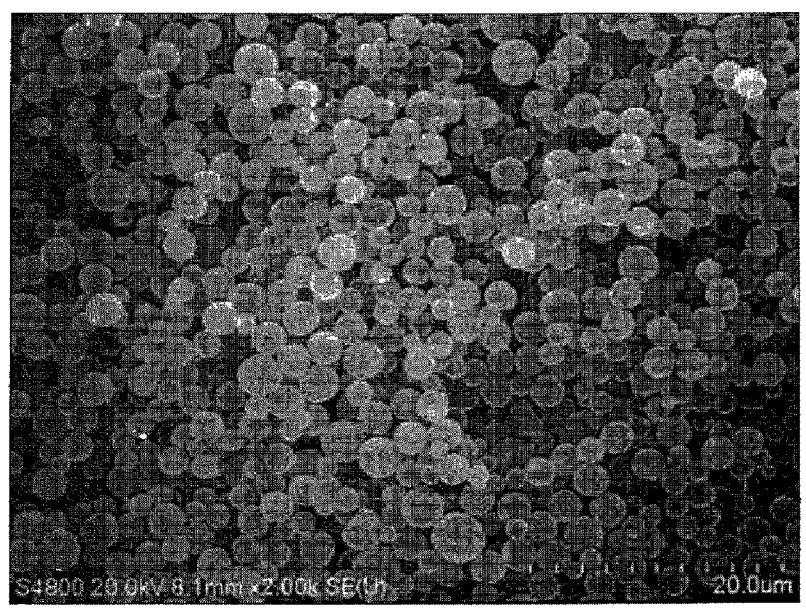
FIG. 2 is an electron microgram of gelatin particles produced in Example 1 of the present invention.

Also, electron micrographs of the dried particles were obtained using an electron microscope (S-4800 (commercial name): Hitachi Inc.) (FIG. 2), and distribution of particle size and particle shape were evaluated. For measuring an average particle diameter, mean volume diameter and mean number diameter, a software for measuring the particle size distribution by image analysis (Macview (commercial name), Mountech Co. Ltd.) was used. As the results, as shown in FIG. 2, the particles obtained had a homogeneous true sphere shape, an average particle diameter of 2.7 µm and the ratio of the mean volume diameter to the mean number diameter of 1.17, and had a narrow particle size distribution. Furthermore, the following evaluation was made for the dispersion solution of particles and dried particles. Results are shown in Table 1.

<Evaluation>

Evaluation of "Particle Dispersion Solution"

The dispersion solution thus obtained was visually evaluated according to the following criteria.

A: a stable dispersion solution was obtained in which no phase separation took place and formation of macroaggregated material was not observed. Also, spontaneously precipitated particles can be re-dispersed easily and did not form tight aggregates.

C: a part or whole polymers aggregated forming macroaggregated materials, and no stable dispersion solution could be obtained.

-: phase separation between the non-aqueous solution and the aqueous solution took place, and no deposition was available.

Evaluation of "Dried Particles"

Electron micrographs of the dried particles were obtained using an electron microscope (S-4800 (commercial name): Hitachi Inc.) and distribution of particle size and particle shape were evaluated according to the following criteria. A software for measuring the particle size distribution by image analysis (Macview (commercial name), Mountech Co. Ltd.) was used.

A: the shape of particles is true sphere, and the ratio of the mean volume diameter to the mean number diameter is 1.25 or smaller.

B: the shape of particles is true sphere, but the ratio of the mean volume diameter to the mean number diameter is 1.5 or larger.

C: evaluation cannot be made because of irregular shaped particles or macroaggregated materials/no deposit.

Examples 2 to 32

A polymer shown in Table 1 or 2 was dissolved in purified water to obtain a polymer solution (the aqueous solutions of the present invention) (step (1)), which was loaded to a printhead of an inkjet printer (Canon, Pixus 950i). Next, 100 g of a solvent shown in Table 1 and 2 was placed in a beaker, and the beaker was placed under the printhead. Then an ejection signal was given to the printhead to eject droplets of the polymer solution into the aforementioned solvent to obtain a mixture solution, and at the same time the polymers were made into particles and dispersed in this mixture (step (2)). The temperature of the mixture at this time was 20° C. for Examples 2, 3, 5 to 7, 9 to 17, and 19 to 32, 30° C. for Examples 3 and 8 and 25° C. for Example 18.

Further, after centrifuging thus obtained dispersion solution at 500 G for 5 minutes, the supernatant was removed and the precipitates were re-suspended by adding 100 ml of 1-butanol. The suspension was centrifuged again at 500 G for 5 minutes and the supernatant was removed. The precipitates were dried under reduced pressure to evaporate residual solvent and water off, and dried particles were obtained. Also, an evaluation was performed for the dispersion solution of particles and dried particles in a similar manner as in Example 1. The results are shown in Tables 1 and 2.

TABLE 1

| | | Production of Particles | | | | Evaluation | |
|---|---|---|---|---|---|---|---|
| | Kind of polymer, concentration | Solvent | Solubility of water in solvent (mass %) | Method for forming particles | Amount of aqueous solution added to solvent | Particle dispersion solution | Dried particles |
| Ex. 1 | Gelatin A, 0.5% | 1-butanol | 20 | Inkjet | 10 g | A | A |
| Ex. 2 | Gelatin A, 0.5% | 2-butanol | 44.1 | Inkjet | 10 g | A | A |
| Ex. 3 | Gelatin B, 0.5% | Isobutyl alcohol | 16.4 | Inkjet | 10 g | A | A |
| Ex. 4 | Gelatin B, 0.5% | 2-pentanol | 8.8 (30° C.) | Inkjet | 4 g | A | A |
| Ex. 5 | Gelatin C, 0.5% | 2-methyl-1-butanol | 8.3 | Inkjet | 4 g | A | A |
| Ex. 6 | Gelatin C, 0.5% | Isopentyl alcohol | 9.7 | Inkjet | 4 g | A | A |
| Ex. 7 | Gelatin D, 0.5% | 1-heptanol | 5.1 | Inkjet | 2 g | A | A |
| Ex. 8 | Gelatin D, 0.5% | tert-pentyl alcohol | 17.7 (30° C.) | Inkjet | 8 g | A | A |
| Ex. 9 | Gelatin E, 0.5% | 3-methyl-2-butanol | 13.5 | Inkjet | 4 g | A | A |
| Ex. 10 | Gelatin E, 0.5% | Cyclohexanone | 9.5 | Inkjet | 4 g | A | A |
| Ex. 11 | Gelatin A, 0.5% | Methylethyl ketone | 9.9 | Inkjet | 4 g | A | A |
| Ex. 12 | Gelatin A, 0.5% | Valeric acid | 13 | Inkjet | 4 g | A | A |
| Ex. 13 | Gelatin B, 0.5% | Methyl acetate | 8 | Inkjet | 4 g | A | A |
| Ex. 14 | Gelatin B, 0.5% | Ethylene glycol monophenyl ether | 10.8 | Inkjet | 4 g | A | A |
| Ex. 15 | Gelatin C, 0.5% | Ethyl acetate | 2.94 | Inkjet | 1 g | A | A |
| Ex. 16 | Gelatin C, 0.5% | 2-heptanone | 1.4 | Inkjet | 0.5 g | A | A |
| Ex. 17 | Gelatin D, 0.5% | Iso-butyric acid | 44.6 | Inkjet | 10 g | A | A |
| Ex. 18 | Gelatin D, 0.5% | Ethyl formate | 17 (25° C.) | Inkjet | 10 g | A | A |
| Ex. 19 | Gelatin E, 0.5% | 1-butanol:2-butanol = 1:1 | —*1 | Inkjet | 10 g | A | A |

The solubility data shown are, unless otherwise specified, the data at 20° C. (Solvent Handbook, Shozo Asahara et al., Kodansha).

*1 solubility unknown (However, since the solubility of water to 1-butanol is 20 mass %, and the solubility of water to 2-butanol is 44.1 mass %, the solubility of water to the 1:1 mixture of these butanols is estimated to be between these solubilities (20 mass % and 44.1 mass %).

TABLE 2

| | | | Production of Particles | | Evaluation | |
|---|---|---|---|---|---|---|
| | Kind of polymer, concentration | Solvent | Solubility of water in solvent (mass %) | Method for forming particles | Amount of aqueous solution added to solvent | Particle dispersion solution | Dried particles |
| Ex. 20 | Bovine serum albumin (Sigma), 0.5% | 2-butanol | 44.1 | Inkjet | 10 g | A | A |
| Ex. 21 | Heparin (Wako Pure Chemical Industries, Ltd.), 0.5% | 2-butanol | 44.1 | Inkjet | 10 g | A | A |
| Ex. 22 | Poly-L-lysine (Sigma), 1% | 2-butanol | 44.1 | Inkjet | 10 g | A | A |
| Ex. 23 | Dextran (Wako Pure Chemical Industries, Ltd.), 1% | 2-butanol | 44.1 | Inkjet | 10 g | A | A |
| Ex. 24 | Polyacrylic Acid (Wako Pure Chemical Industries, Ltd.), 1% | 2-butanol | 44.1 | Inkjet | 10 g | A | A |
| Ex. 25 | Insulin (Sigma), 4 mg/ml | 2-butanol | 44.1 | Inkjet | 10 g | A | A |
| Ex. 26 | Horse Radish Peroxidase (Fluka), 5 mg/ml | 2-butanol | 44.1 | Inkjet | 10 g | A | A |
| Ex. 27 | Water dispersed polyester (Toyobo), 0.5% | 2-butanol | 44.1 | Inkjet | 10 g | A | A |
| Ex. 28 | Pullulan (Wako Pure Chemical Industries, Ltd.), 1% | 2-butanol | 44.1 | Inkjet | 10 g | A | A |
| Ex. 29 | EGFP Expressing Plasmid DNA, 5 mg/ml | 2-butanol | 44.1 | Inkjet | 10 g | A | A |
| Ex. 30 | DNA-Gelatin Complex | 2-butanol | 44.1 | Inkjet | 10 g | A | A |
| Ex. 31 | Resin A, 1% | 2-butanol | 44.1 | Inkjet | 10 g | A | A |
| Ex. 32 | Pigment resin dispersion solution | 2-butanol | 44.1 | Inkjet | 10 g | A | A |

The solubility data shown are, unless otherwise specified, the data at 20° C. (Solvent Handbook, Shozo Asahara et al., Kodansha).

Example 33

Gelatin A (Polymer) was dissolved in purified water to prepare 0.5% aqueous gelatin solution (the aqueous solution of the present invention) (Step (a)). Next, the polymer solution was slowly added to 100 g of 1-butanol (solvent) while stirring with a magnetic stirrer and the stirring was continued for 10 minutes. During this step, the polymer was made into a particle form and dispersed (step (b)) in the mixture.

Figure 3:
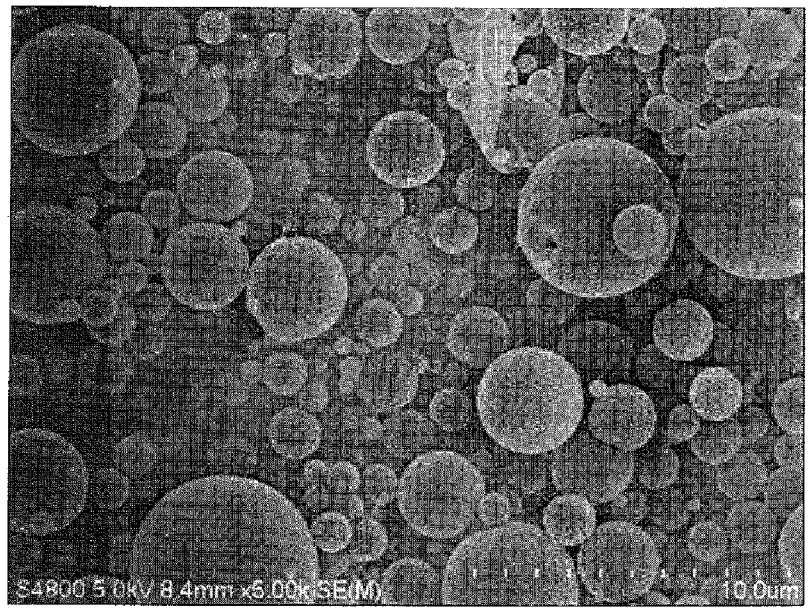
FIG. 3 is an electron microgram of gelatin particles produced in Example 33 of the present invention.

Next, the dispersion solution thus obtained was centrifuged at 500 G for 5 minutes, the supernatant was removed and the precipitates were resuspended in 100 ml of 1-butanol. The suspension was again centrifuged at 500 G for 5 minutes and the precipitates were obtained after removing the supernatant. These precipitates were dried under reduced pressure to remove the residual solvent to obtain the dried particles. Also, electron micrographs of the dried particles were obtained using an electron microscope (S-4800 (commercial name): Hitachi Inc.) (FIG. 3). Evaluation for the particle dispersion solution and dried particles was performed as in Examples 2-20. Results are shown in Table 3.

Examples 34 to 43

A polymer shown in Table 3 was dissolved in purified water to prepare a polymer solution (the aqueous solution of the present invention) (Step (a)). Next, the polymer solution was slowly added to 100 g of a solvent shown in Table 1 while stirring with a magnetic stirrer and the stirring was continued for 10 minutes. During this step, the polymer was made into a particle form and dispersed (step (b)) in the mixture.

Next, the dispersion solution thus obtained was centrifuged at 500 G for 5 minutes, the supernatant was removed and the precipitates were resuspended in 100 ml of 1-butanol. The suspension was again centrifuged at 500 G for 5 minutes and the precipitates were obtained after removing the supernatant. These precipitates were dried under reduced pressure to remove the residual solvent to obtain the dried particles. Evaluation for the particle dispersion solution and dried particles was performed as in Examples 2 to 20. Results are shown in Table 3.

Comparative Examples 1 to 10

A mixture of an aqueous solution and a solvent, and dried particles were obtained by a similar method as Example 1 or 33 except that a polymer and a solvent shown in Table 4 were used. These were evaluated as in the aforementioned Examples 2 to 20. Results are shown in Table 4. Here, the temperature of the mixture was 20° C. for Comparative Examples 1 to 5, 7, 8 and 10, 25° C. for Comparative Example 6 and 30° C. for Comparative Example 9. Also, when particles were produced in Comparative Examples 8 to 10, the aqueous solution was mixed to the solvent so that the amount of water in the aqueous solution exceeds the amount soluble to the solvent.

Example 44

Cross-linked dried particles were obtained by treating the dried particles produced in Example 9 in a vacuum oven at 160° C. for 72 hours. When the cross-linked dried particles thus obtained were mixed with ion exchanged water and stirred, an aqueous dispersion of the cross-linked particles could be obtained without dissolving the particles.

Example 45

The dried particles produced in Example 1 were suspended in a small amount of acetone, mixed with 1% glutaraldehyde aqueous solution and stirred at 4° C. for 24 hours, and then centrifuged at 500 G for 5 minutes. After removing the supernatant, 0.1 M glycine aqueous solution was added to the precipitates and the mixture was stirred at room temperature for 1 hour. After centrifuging at 500 G for 5 minutes, the supernatant was removed, ion exchanged water was added to the precipitates and the mixture was stirred. As the results, an aqueous dispersion of the cross-linked particles could be obtained without dissolving particles.

Example 46

500 mg of the dried particles produced in Example 8 was dispersed in a small amount of acetone (100 ml), and to this 20 ml of hexamethylene diisocyanate was added dropwise and a cross-link reaction was performed for 5 hours at room temperature. The cross-linked particles were obtained by washing the reaction mixture with acetone and purified water and by freeze drying. Next, these cross-linked particles were centrifuged at 500 G for 5 minutes, the supernatant was removed and ion exchanged water was added to the precipitates and stirred. As the results, an aqueous dispersion of the cross-linked particles could be obtained without dissolving particles.

Example 47

A plasmid DNA was labeled with rhodamine using a Rhodamine labeling kit (Mirus) according to the protocol. Next, an aqueous solution of plasmid DNA of the luciferase gene (bioactive substance) labeled with rhodamine was added to the aqueous dispersion of cross-linked particles produced in Example 44 and pipetted to produce a particle-DNA complex solution. Observation of thus produced particle-DNA complex solution using a fluorescent microscope revealed that the surface of the particles was overlapped with the fluorescent image of rhodamine confirming that the plasmid DNA was held on the particles.

Example 48

5 µl of $Na^{125}I$ (NEZ033 (commercial name), PerkinElmer Inc.) and 100 µl of potassium phosphate buffer solution of chloramine T (Nacalai Tesque Co. Ltd.) (0.2 mg/ml) were added to 200 µl of potassium phosphate buffer solution of basic fibroblast growth factor (bFGF (commercial name), R & D Inc.) (0.5 mg/ml), and the mixture was stirred for 2 minutes. Then, 4 mg/ml of disodium disulfite (Nacalai Tesque Co. Ltd.) was added, stirred for 2 minutes, and then free radioactive iodine and radiolabeled bFGF were separated using a gel chromatography column (PD-10, GE Healthcare (commercial name), Bioscience Co. Ltd.) to produce radiolabeled bFGF (labeling substance).

Next, the aqueous dispersion of the cross-linked particles produced in Example 46 was mixed with the aqueous solution of the radiolabeled bFGF described above and pipetting was performed to produce a particle-bFGF suspension. The suspension was centrifuged at 500 G for 5 minutes and the radioactivity of the precipitates was measured by a gamma counter (PerkinElmer Co. Ltd.). It was found that the precipitates had radioactivity confirming that bFGF was held in the particles.

Example 49

After placing the dried particles produced in Example 47 in a vacuum chamber and evacuating, perfluoropropane (Wako Pure Chemical Industries, Ltd.) was introduced in the vacuum chamber to impregnate the particles with perfluoropropane. These particles were suspended in an aqueous solution and an ultrasound image of the particles was obtained using an ultrasound imaging apparatus. The image having enhanced contrast could be obtained due to the presence of the particles.

TABLE 3

| | | | Production of Particles | | | Evaluation | |
|---|---|---|---|---|---|---|---|
| | Kind of polymer, concentration | Solvent | Solubility of water in solvent (mass %) | Method for forming particles | Amount of aqueous solution added to solvent | Particle dispersion solution | Dried particles |
| Ex. 33 | Gelatin A, 0.5% | 1-butanol | 20 | Magnetic stirrer | 10 g | A | B |
| Ex. 34 | Gelatin B, 0.5% | 2-butanol | 44.1 | Magnetic stirrer | 10 g | A | B |
| Ex. 35 | Gelatin C, 0.5% | Isobutyl alcohol | 16.4 | Magnetic stirrer | 5 g | A | B |
| Ex. 36 | Gelatin D, 0.5% | tert-pentyl alcohol | 17.7 (30° C.) | Magnetic stirrer | 5 g | A | B |

TABLE 3-continued

| | Kind of polymer, concentration | Solvent | Solubility of water in solvent (mass %) | Method for forming particles | Amount of aqueous solution added to solvent | Particle dispersion solution | Dried particles |
|---|---|---|---|---|---|---|---|
| Ex. 37 | Gelatin E, 0.5% | Cyclohexanone | 9.5 | Magnetic stirrer | 5 g | A | B |
| Ex. 38 | Pullulan (Wako Pure Chemical Industries, Ltd.), 1% | 2-butanol | 44.1 | Magnetic stirrer | 10 g | A | B |
| Ex. 39 | Dextran (Sigma), 1% | Methylethyl ketone | 9.9 | Magnetic stirrer | 4 g | A | B |
| Ex. 40 | Insulin (Sigma), 4 mg/ml | Methyl acetate | 8 | Magnetic stirrer | 4 g | A | B |
| Ex. 41 | Bovine serum albumin (Sigma), 0.5% | 2-butanol | 44.1 | Magnetic stirrer | 10 g | A | B |
| Ex. 42 | Poly-L-lysine (Sigma), 1% | 2-butanol | 44.1 | Magnetic stirrer | 10 g | A | B |
| Ex. 43 | Pullulan (Wako Pure Chemical Industries, Ltd.), 1% | 2-butanol | 44.1 | Magnetic stirrer | 10 g | A | B |

TABLE 4

| | Kind of polymer, concentration | Solvent | Solubility of water in solvent (mass %) | Method for forming particles | Amount of aqueous solution added to solvent | Particle dispersion solution | Dried particles |
|---|---|---|---|---|---|---|---|
| Com. Ex. 1 | Gelatin A, 0.5% | Acetone | ∞ | Inkjet | 10 g | C | C |
| Com. Ex. 2 | Gelatin B, 0.5% | tert-butanol | ∞ | Inkjet | 10 g | C | C |
| Com. Ex. 3 | Gelatin C, 0.5% | ethanol | ∞ | Magnetic stirrer | 10 g | C | C |
| Com. Ex. 4 | Gelatin D, 0.5% | Glycolmonomethyl ether | ∞ | Magnetic stirrer | 10 g | C | C |
| Com. Ex. 5 | Gelatin E, 0.5% | 2-octanol | 0.1 or less | Inkjet | 10 g | — | C |
| Com. Ex. 6 | Gelatin A, 0.5% | Dipropyl ether | 0.68 (25° C.) | Magnetic stirrer | 10 g | — | C |
| Com. Ex. 7 | Gelatin B, 0.5% | 4-heptanone | 0.87 | Magnetic stirrer | 10 g | — | C |
| Com. Ex. 8 | Gelatin C, 0.5% | 1-heptanol | 5.1 | Magnetic stirrer | 10 g | — | C |
| Com. Ex. 9 | Gelatin D, 0.5% | 2-pentanol | 8.8 (30° C.) | Magnetic stirrer | 20 g | — | C |
| Com. Ex. 10 | Gelatin E, 0.5 | 1-butanol | 20 | Magnetic stirrer | 40 g | — | C |

The solubility data shown are, unless otherwise specified, the data at 20° C. (Solvent Handbook, Shozo Asahara et al., Kodansha)

<Membrane Emulsification/Microchannel Emulsification/Branching Microchannel Method>

Example 50

100 g of 1-butanol (solvent; solubility of water in the solvent=20 mass %) was placed in a beaker. Gelatin A (polymer) was dissolved in pure water to obtain 0.5% gelatin aqueous solution (the aqueous solution of the present invention (step (1)), and then this was set to an Internal Pressure Type Membrane Emulsification Micro Unit (SPG pore diameter: 1.2 µm) (SPG Technology Co. Ltd.) and the SPG membrane was immersed in 1-butanol. Subsequently the aqueous solution of gelatin was pushed into 1-butanol through SPG membrane by pressuring the membrane emulsifier micro unit to obtain a dispersion liquid of gelatin A particles (mixture solution) as well as forming gelatin A particles in the mixture solution (step (2)). At this time the temperature of the mixture solution was 20° C.

Further, the dispersion liquid thus obtained was centrifuged at 500 G for 5 minutes, the supernatant was removed and the precipitates were resuspended in 100 ml of 1-butanol. The suspension was again centrifuged at 500 G for 5 minutes, the supernatant was removed and then the precipitates were dried under reduced pressure to remove residual solvent and water and to obtain dried particles. Also, the dispersion liquid of the particles and the dried particles were evaluated as in Example 1. The results are shown in Table 5.

Example 51

Gelatin A (polymer) was dissolved in pure water to obtain 0.5% gelatin aqueous solution (the aqueous solution of the present invention) (step (1)), and this was used as a dispersion phase of a microchannel emulsifier made by EP Tech Co. Ltd. (slit size: 10 µm×100 µm) and flowed at a rate of 4 ml/minutes and 1-butanol (solvent; solubility of water to the solvent=20 mass %) flowed at a rate of 2 ml/minutes as a continuous phase. By this procedure, the gelatin aqueous solution was pushed into 1-butanol to obtain a dispersion liquid of gelatin A particles (mixture solution) as well as forming gelatin A particles in the mixture solution (step (2)). At this time the temperature of the mixture solution was 20° C.

Further, the dispersion liquid thus obtained was centrifuged at 500 G for 5 minutes, the supernatant was removed and the precipitates were resuspended in 100 ml of 1-butanol. The suspension was again centrifuged at 500 G for 5 minutes, the supernatant was removed and then the precipitates were dried under reduced pressure to remove residual solvent and water and to obtain dried particles. Also, the dispersion liquid of the particles and the dried particles were evaluated as in Example 1. The results are shown in Table 5.

Example 52

Gelatin A (polymer) was dissolved in pure water to obtain 0.5% gelatin aqueous solution (the aqueous solution of the present invention) (step (1)). A micropath was prepared in which micropath 2 (width: 10 µm) is connected to micropath 1 (width: 15 µm) in right angle. 1-butanol and the gelatin aqueous solution were introduced to micropaths 1 and 2 and flowed at the rate of 0.1 m/s and 0.01 m/s, respectively using microsyringe pumps. By this procedure, the gelatin aqueous solution was pushed into 1-butanol to obtain a dispersion liquid of gelatin A particles (mixture solution) as well as forming gelatin A particles in the mixture solution (step (2)). At this time the temperature of the mixture solution was 20° C.

Further, the dispersion solution thus obtained was centrifuged at 500 G for 5 minutes, the supernatant was removed and the precipitates were resuspended in 100 ml of 1-butanol. The suspension was again centrifuged at 500 G for 5 minutes, the supernatant was removed and then the precipitates were dried under reduced pressure to remove residual solvent and water and to obtain dried particles. Also, the dispersion liquid of the particles and the dried particles were evaluated as in Example 1. The results are shown in Table 5.

TABLE 5

| | Production of Particles | | | | | Evaluation | |
|---|---|---|---|---|---|---|---|
| | Kind of polymer, concentration | Solvent | Solubility of water in solvent (weight %) | Method for forming particles | Amount of aqueous solution added to solvent | Particle dispersion solution | Dried particles |
| Ex. 50 | Gelatin A, 0.5% | 2-butanol | 20 | Membrane emulsifying micro unit | 10 g | A | A |
| Ex. 51 | Gelatin A, 0.5% | 2-butanol | 20 | Microchannel emulsifying apparatus | 10 g | A | A |
| Ex. 52 | Gelatin A, 0.5% | 2-butanol | 20 | Micropath | 10 g | A | A |

Example 53

Gelatin A (polymer) was dissolved in the water dispersed polyester solution used in Example 28 to obtain 0.5% gelatin-polyester mixed solution. A dispersion liquid (mixture solution) of particles including gelatin A-polyester complex and dried particles were obtained by the similar steps as in Example 1 except that the gelatin A aqueous solution in Example 1 was replaced with this gelatin-polyester mixed aqueous solution.

By suspending the dried particles thus obtained in ion exchanged water, an aqueous dispersion of gelatin-polyester particles without the particles being dissolved.

Example 54

A dispersion liquid (mixture solution) of particles including gelatin A-PLGA complex and dried particles were obtained by the similar steps as in Example 53 except that the water dispersed polyester solution in Example 53 was replaced with the PLGA dispersion that was produced in the production example. By suspending the dried particles thus obtained in ion exchanged water, an aqueous dispersion of gelatin-PLGA particles without the particles being dissolved.

Example 55

A dispersion liquid (mixture solution) of particles including gelatin A-PLGA-paclitaxel complex and dried particles were obtained by the similar steps as in Example 53 except that the water dispersed polyester solution in Example 53 was replaced with the PLGA-paclitaxel dispersion that was produced in the production example. Observation of thus obtained dried particles using a fluorescent microscope revealed that the particles was overlapped with the fluorescent image of Oregon Green confirming that paclitaxel was held in the particles.

When particles were produced in Examples 1 to 43 and 50 to 54, the aqueous solution was added or mixed to the solvent as droplets in such an amount that entire water in the solution was dissolved in the solvent. Also, when particles were produced in Comparative Examples 8 to 10, the aqueous solution was mixed to the solvent in such an amount that water in the solution exceeded the amount could be solubilized in the solvent.

It is seen from the results shown in Tables 1 to 5 that in the cases of Examples 1 to 43 and Examples 50 to 54 where the particles were produced using the method for the production of the present invention, all the particle dispersion was "A". It is also seen that the evaluation for the dried particles were "A" or "B".

On the other hand, in the cases of Comparative Examples 1 to 10 where the production method of particles of the present invention was not used, the particle dispersions were evaluated to be "C" or "-" and the dried particles were evaluated to be "C". From these results it is understood that by using the production method of the present invention, good evaluation for the particle dispersion and dried particles could be obtained.

<Production of Magnetic Particles>

Example 56

4 g of gelatin A (derived from bovine bone, isoelectric point 5.0) was dissolved in purified water and mixed with a mixture aqueous solution of 8 g of ferrous chloride tetrahydrate (Wako Pure Chemical Industries, Ltd.) and 20 g of ferric chloride hexahydrate (Wako Pure Chemical Industries, Ltd.). Next, ammonia water was added to this mixture solution and reacted at 40° C. for 20 minutes to deposit ferrous oxide (magnetic material) and then the mixture was desalted a desalting column (PD-10, GE Health Care (commercial name), Bioscience Co. Ltd.) to produce a suspension of microparticles of ferrous oxide. The average particle diameter of the microparticles of ferrous oxide was measured using a dynamic light scattering apparatus (DLS-7000 (commercial name), Otsuka Electronics Co. Ltd.) to be 155 nm.

The suspension of ferrous oxide microparticles was loaded to a printhead of an inkjet printer (Canon, Pixus 950i (commercial name)). Next, 100 g of 2-butanol (solvent; the solubility of water to this solvent=44.1 mass %) was placed in a beaker, and the beaker was placed under the printhead.

An ejection signal was given to the printhead to eject droplets of the gelatin solution and 10 g of the solution was ejected into 2-butanol. By making biodegradable polymer and magnetic material (ferrous oxide) into particles in the mixture, magnetic particles which were aggregates of microparticles of ferrous oxide were obtained. Also, a dispersion liquid was obtained in which these magnetic particles were dispersed. The dispersion liquid thus obtained was centrifuged at 500 G for 5 minutes, and the precipitates were obtained after removing the supernatant. The precipitates were dried under reduced pressure to distill the residual solvent off to obtain dried magnetic particles. These dried magnetic particles were placed in a vacuum oven (Espec Corp.) and treated at 160° C. for 12 hours to obtain incompletely cross-linked magnetic particles.

Figure 4:
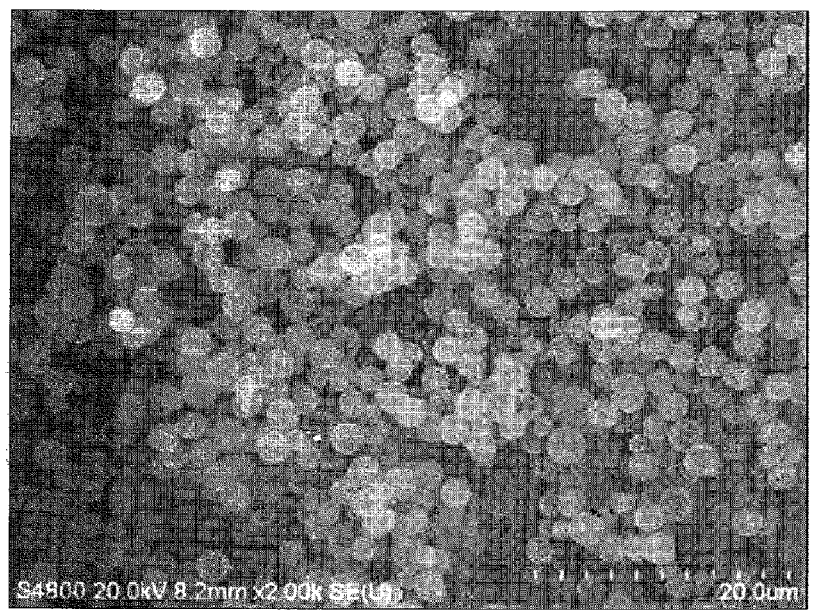
FIG. 4 is an electron microgram of magnetic particles produced in Example 56 of the present invention.

Electron micrographs of the dried magnetic particles were obtained using an electron microscope (S-4800 (commercial name): Hitachi Inc.) (FIG. 4), and distribution of particle size and particle shape were evaluated. For measuring an average particle diameter, mean volume diameter and mean number diameter, a software for measuring the particle size distribution by image analysis (Macview (commercial name), Mountech Co. Ltd.) was used. The particles obtained had a homogeneous true sphere shape, an average particle diameter of 2.4 μm and the ratio of the mean volume diameter to the mean number diameter of 1.11, and had a narrow particle size distribution.

Example 57

20 g of gelatin B (derived from pig skin, isoelectric point 9.0) was dissolved in 500 ml of phosphate buffer and heated to 40° C., and then 60 ml of ethylenediamine (Nacalai Tesque Co. Ltd.) was added to this solution to adjust pH at 5.0. Next, 10 g of 1-ethyl-3-(3-dimethylaminopropyl) carbodiimide hydrochloride (Nacalai Tesque Co. Ltd.) was added and reacted for 24 hours. The mixture was dialyzed for 3 days and freeze dried to produce ethylenediamine introduced gelatin (biodegradable polymer).

A ferrous oxide microparticle suspension was produced by the same method as Example 56 except that gelatin in Example 56 was replaced with the ethylenediamine introduced gelatin described above, and the dispersion liquid of magnetic particles and dried particles were obtained using this by the same method as Example 56. These dried magnetic particles were placed in a vacuum oven (Espec Corp.) and treated at 160° C. for 12 hours to obtain incompletely cross-linked magnetic particles.

Example 58

Each of 10 g of Gelatin A (derived from beef bone, isoelectric point 5.0) and 3.5 g of MeO-PEG-NHS (MEC-50HS, NOF Corporation) was dissolved in DMSO, mixed and stirred at room temperature for 1 hour. The mixture was dialyzed for 3 days and freeze dried to produce PEG gelatin (biodegradable polymer).

A ferrous oxide microparticle suspension was produced by the same method as Example 56 except that gelatin in Example 56 was replaced with the PEG gelatin described above, and the dispersion liquid of magnetic particles and dried particles were obtained using this by the same method as Example 56. These dried magnetic particles were placed in a vacuum oven (Espec Corp.) and treated at 160° C. for 12 hours to obtain incompletely cross-linked magnetic particles.

Example 59

A ferrous oxide microparticle suspension was produced by the same method as Example 56 except that gelatin in Example 56 was replaced with a mixture of an equal volume of ferrous oxide microparticles suspensions produced in Example 56 and Example 58, and the dispersion liquid of magnetic particles and dried particles were obtained using this by the same method as Example 56.

500 mg of dried magnetic powders produced in Example 59 was dispersed in 100 ml acetone, and to this 5 ml of hexamethylene diisocyanate was added dropwise and reacted at room temperature for 15 minutes. The reaction product was washed with acetone, further with purified water and then freeze dried to obtain incompletely cross-linked magnetic particles.

<Evaluation of Incomplete Cross-Link>

The incompletely cross-linked particles produced in Examples 56 to 59 were suspended in water, and subjected to sonication for 5 minutes by placing a probe of an ultrasonic generator (UR-20P (commercial name), Tomy Seiko Co. Ltd.) (external stimulation). Next, each of the particle suspension before and after the sonication treatment was placed in a clear glass vial and a ferrite magnet was contacted to each vial, and after standing the dispersion liquids for 15 minutes, the state of particles was visually observed.

As the results, it was confirmed that in the suspension before the sonication treatment, particles accumulated to the side where the ferrite magnet was contacted. An observation by a phase contrast microscope revealed many particles in the part of the suspension which was accumulated on the side where the ferrite magnet was contacted. On the other hand, no reaction was observed for the suspension after the sonication treatment. Furthermore, no particle was confirmed in the suspension after the sonication by the phase contrast microscope observation. These results confirmed that the magnetic particles were disintegrated by the sonication treatment (external stimulation).

<Confirmation of Controlled Drug Release>

Example 60

5 μl of $Na^{125}I$ (NEZ033 (commercial name), PerkinElmer Inc) and 100 μl of potassium phosphate buffer solution of chloramine T (Nacalai Tesque Co. Ltd.) (0.2 mg/ml) were added to 200 μl of potassium phosphate buffer solution of basic fibroblast growth factor (bFGF (commercial name), R & D Inc.) (0.5 mg/ml), and the mixture was stirred for 2 minutes. Then, 4 mg/ml of disodium disulfite (Nacalai Tesque Co. Ltd.) was added, stirred for 2 minutes, and then free radioactive iodine and radiolabeled bFGF were separated using a gel chromatography column (PD-10, GE Healthcare (commercial name), Bioscience Co. Ltd.) to produce radio-labeled bFGF (labeling substance).

Next, the aqueous dispersion of the incompletely cross-linked magnetic particles produced in Example 56 was mixed with the radiolabeled bFGF aqueous solution and pipetted to produce magnetic particle-bFGF suspension. The magnetic particle-bFGF suspension was centrifuged at 500 G for 5 minutes and the radioactivity of the precipitates was measured by a gamma counter (PerkinElmer Co. Ltd.). It was found that the precipitates had radioactivity confirming that bFGF was held in the particles.

Further, the magnetic particle-bFGF suspension was sonicated for 5 minutes by placing a probe of an ultrasonic generator (UR-20P (commercial name), Tomy Seiko Co. Ltd.). Next, the suspension was placed in a clear glass vial, a ferrite magnet was contacted to the vial, and after standing for 15 minutes, the dispersion liquids were visually observed. No particular change in the suspension was observed. This result confirms that the magnetic particles were disintegrated by the sonication (external stimulation).

Furthermore, each of the non-sonicated suspension and sonicated suspension was centrifuged at 500 G for 5 minutes and the radioactivity of the supernatant was compared. It was found that the radioactivity of the sonicated supernatant was markedly higher.

Example 61

EGFP expression plasmid DNA was labeled with rhodamine using a Rhodamine labeling kit (Mirus) according to the protocol. An aqueous solution of rhodamine labeled EGFP expression plasmid DNA (bioactive substance) was added to the aqueous dispersion of the incompletely cross-linked magnetic particles produced in Example 57 and pipetted to produce the magnetic particle-DNA complex suspension. Observation of thus produced magnetic particle-DNA complex suspension using a fluorescent microscope yielded an image of the rhodamine fluorescent image overlapping the surface of the particles confirming that the plasmid DNA is held on the particles.

Further, the magnetic particle-DNA complex solution was sonicated for 5 minutes by placing a probe of an ultrasonic generator (UR-20P (commercial name), Tomy Seiko Co. Ltd.). Next, the suspension was placed in a clear glass vial, a ferrite magnet was contacted to the vial, and after standing for 15 minutes, the suspension was visually observed. No particular change in the suspension was observed. This result confirms that the magnetic particles were disintegrated by the sonication (external stimulation).

Furthermore, each of the non-sonicated suspension and sonicated suspension was centrifuged at 500 G for 5 minutes and the fluorescence intensity of the supernatant was compared using a fluorescent microplate reader (Gemini EM, Japan Molecular Devices Corporation; for the analyses of average particle diameter, mean volume diameter and mean number diameter, a software for measuring the particle size distribution by image analysis (Macview, Mountech Co. Ltd.) was used). It was found that the fluorescent intensity of the sonicated supernatant was markedly higher.

Example 62

Cisplatin (bioactive substance; Nippon Kayaku Co. Ltd.) was treated with an ultrasonic homogenizer (Ultrasonic generator Model US150 (commercial name), Nissei) to prepare 2 mg/ml of an aqueous solution of cisplatin. Next, the magnetic particles produced in Example 56 was suspended in water, mixed with the aqueous solution of cisplatin to prepare a suspension of magnetic particle suspension containing magnetic particle-cisplatin.

The suspension thus produced was sonicated for 5 minutes by placing a probe of an ultrasonic generator (UR-20P (commercial name), Tomy Seiko Co. Ltd.). Next, the sonicated suspension was centrifuged at 500 G for 5 minutes, and the supernatant was subjected to measurement using an atomic absorption apparatus (Hitachi Model Z-8000 (commercial name), Hitachi Co. Ltd.). It was confirmed that cisplatin was released because platinum was detected in the supernatant.

Example 63

A ferrous oxide microparticle suspension was produced by the same method as Example 56 except that gelatin in Example 56 was replaced with pullulan (biodegradable polymer; Wako Pure Chemical Industries, Ltd.) and that incomplete cross-linking was not performed, and the dispersion liquid of magnetic particles and dried magnetic particles were obtained using this by the same method as Example 56.

Example 64

A ferrous oxide microparticle suspension was produced by the same method as Example 56 except that gelatin in Example 56 was replaced with dextran (biodegradable polymer; Wako Pure Chemical Industries, Ltd.) and that incomplete cross-linking was not performed, and the dispersion liquid of magnetic particles and dried magnetic particles were obtained using this by the same method as Example 56. Electron micrographs taken by an electron microscope (S-4800, Hitachi Co. Ltd.) revealed that the good magnetic particles having a true spherical form could be obtained.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2006-317184, filed Nov. 24, 2006, which is hereby incorporated by reference herein in its entirety.

The invention claimed is:

1. A method for producing particles comprising the steps of:
   (1) preparing an aqueous solution comprising one or more polymers; and
   (2) introducing the aqueous solution as droplets into a solvent capable of dissolving water by 1 mass % or more and less than 50 mass %,
   the method further comprising the step of obtaining particles containing the one or more polymers in the solvent,
   wherein, in the step (2), a procedure for introducing the aqueous solution as droplets into the solvent is a procedure for discharging the aqueous solution into the solvent from pores by contacting a membrane having pores with the pore area of 0.01 um$^2$ or more and 5000 um$^2$ or less with the solvent.

2. A method for producing particles comprising the steps of:
   (1) preparing an aqueous solution comprising one or more polymers; and
   (2) introducing the aqueous solution as droplets into a solvent capable of dissolving water by 1 mass % or more and less than 50 mass %,
   the method further comprising the step of obtaining particles containing the one or more polymers in the solvent,
   wherein, in the step (2), a procedure for introducing the aqueous solution as droplets into the solvent is an introduction process of the aqueous solution which is flowing in a second microchannel at a constant rate merging to the solvent which is flowing in a first microchannel at a constant rate.

3. A method for producing particles comprising the steps of:
   (1) preparing an aqueous solution comprising one or more polymers; and
   (2) introducing the aqueous solution as droplets into a solvent capable of dissolving water by 1 mass % or more and less than 50 mass %,
   the method further comprising the step of obtaining particles containing the one or more polymers in the solvent,
   wherein, in the step (2), an amount of the aqueous solution introduced into the solvent is controlled so that all the water in the aqueous solution is dissolved in the solvent.

4. A method for producing particles comprising the steps of:
   (a) preparing an aqueous solution comprising one or more polymers; and
   (b) mixing the aqueous solution to a solvent capable of dissolving water by 1 mass % or more and less than 50 mass % so that (water mass)/(total mass of solvent and water)×100 is equal to or less than the solubility of water in the solvent to form the one or more polymers into dispersed particles in a mixture of the aqueous solution and the solvent.

5. The method for producing particles according to claim 4, wherein the step (b) comprises:
   introducing the aqueous solution into the solvent; and
   stirring a mixed solution of the aqueous solution and the solvent.

6. The method for producing particles according to claim 4, wherein, in the step (b), an amount of the aqueous solution mixed with the solvent is controlled so that an amount of the one of more polymers is over a dissolvable amount to the mixed solution.

7. The method for producing particles according to claim 4, wherein the solvent is a solvent capable of dissolving water by 7.5 mass % or more and less than 50 mass %.

8. The method for producing particles according to claim 4, further comprising removing the water and the solvent from a mixed solution after the step of forming the one or more polymers into the dispersed particles in the mixture.

9. The method for producing particles according to claim 4, further comprising cross-linking the one or more polymers during or after the step of forming the one or more polymers into the dispersed particles.

10. A method for producing particles comprising the steps of:
    (1) preparing an aqueous solution comprising one or more polymers; and
    (2) introducing the aqueous solution as droplets into a solvent capable of dissolving water by 1 mass % or more and less than 50 mass %,
    the method further comprising the step of obtaining particles containing the one or more polymers in the solvent,
    wherein particles comprising a water soluble polymer and a water insoluble polymer are formed into dispersed particles by using a mixed solution comprising at least one or more water soluble polymers as the aqueous solution and at least one or more water insoluble polymers dispersed.

11. The method for producing particles according to claim 10, wherein the one or more polymers are biodegradable.

12. The method for producing particles according to claim 10, wherein the water soluble polymer comprises at least gelatin or a gelatin derivative.

13. The method for producing particles according to claim 10, wherein the water insoluble polymer is selected from the group comprising polylactic acid, polycaprolactone or copolymer of polylactic acid and glycolic acid.

14. A method for producing particles comprising the steps of:
   (1) preparing an aqueous solution comprising one or more polymers; and
   (2) introducing the aqueous solution as droplets into a solvent capable of dissolving water by 1 mass % or more and less than 50 mass %,
   the method further comprising the step of obtaining particles containing the one or more polymers in the solvent,
   wherein particles comprising the one or more polymers and at least any one of a bioactive substance and a labeling substance are formed into dispersed particles by using an aqueous solution comprising the at least any one of the bioactive substance and the labeling substance as the aqueous solution or by using a solvent comprising the at least any one of the bioactive substance and the labeling substance as the solvent.

15. A method for producing magnetic particles comprising the steps of:
   (1) preparing an aqueous solution comprising one or more polymers; and
   (2) introducing the aqueous solution as droplets into a solvent capable of dissolving water by 1 mass % or more and less than 50 mass %,
   the method further comprising the step of obtaining particles containing the one or more polymers in the solvent,
   wherein the one or more polymers comprise at least one or more water soluble polymers, and
   wherein magnetic particles comprising at least the one or more polymers and a magnetic material can be obtained in a step of forming the one or more polymers and the magnetic material into dispersed particles in a mixture of the aqueous solution and the solvent by using an aqueous solution comprising at least the magnetic material as the aqueous solution.

16. The method for producing magnetic particles according to claim 15, further comprising performing incomplete cross-linking to the magnetic particles at a time of mixing the aqueous solution to the solvent or after obtaining the magnetic particles comprising the one or more polymers and the magnetic material.

17. The method for producing particles according to claim 4, wherein the solvent comprises at least one substance selected from the group consisting of 1-butanol, 2-butanol, isobutyl alcohol, 2-pentanol, 3-pentanol, 2-methyl-1-butanol, isopentyl alcohol, tert-pentyl alcohol, 3-methyl-2-butanol, phenol, cyclohexanol, cyclohexanone, methylethyl ketone, isobutyric acid, valeric acid, methyl formate, ethyl formate, propyl formate, methyl acetate, ethyleneglycol monophenyl ether, propionic acid nitrile, and triethyl amine.

18. The method for producing particles according to claim 1, wherein the solvent is a solvent capable of dissolving water by 7.5 mass % or more and less than 50 mass %.

19. The method for producing particles according to claim 1, wherein the solvent comprises at least one substance selected from the group consisting of 1-butanol, 2-butanol, isobutyl alcohol, 2-pentanol, 3-pentanol, 2-methyl-1-butanol, isopentyl alcohol, tert-pentyl alcohol, 3-methyl-2-butanol, phenol, cyclohexanol, cyclohexanone, methylethyl ketone, isobutyric acid, valeric acid, methyl formate, ethyl formate, propyl formate, methyl acetate, ethyleneglycol monophenyl ether, propionic acid nitrile, and triethyl amine.

20. The method for producing particles according to claim 2, wherein the solvent is a solvent capable of dissolving water by 7.5 mass % or more and less than 50 mass %.

21. The method for producing particles according to claim 2, wherein the solvent comprises at least one substance selected from the group consisting of 1-butanol, 2-butanol, isobutyl alcohol, 2-pentanol, 3-pentanol, 2-methyl-1-butanol, isopentyl alcohol, tert-pentyl alcohol, 3-methyl-2-butanol, phenol, cyclohexanol, cyclohexanone, methylethyl ketone, isobutyric acid, valeric acid, methyl formate, ethyl formate, propyl formate, methyl acetate, ethyleneglycol monophenyl ether, propionic acid nitrile, and triethyl amine.

22. The method for producing particles according to claim 3, wherein the solvent is a solvent capable of dissolving water by 7.5 mass % or more and less than 50 mass %.

23. The method for producing particles according to claim 3, wherein the solvent comprises at least one substance selected from the group consisting of 1-butanol, 2-butanol, isobutyl alcohol, 2-pentanol, 3-pentanol, 2-methyl-1-butanol, isopentyl alcohol, tert-pentyl alcohol, 3-methyl-2-butanol, phenol, cyclohexanol, cyclohexanone, methylethyl ketone, isobutyric acid, valeric acid, methyl formate, ethyl formate, propyl formate, methyl acetate, ethyleneglycol monophenyl ether, propionic acid nitrile, and triethyl amine.

* * * * *